(12) United States Patent
Apodaca et al.

(10) Patent No.: US 7,541,359 B2
(45) Date of Patent: Jun. 2, 2009

(54) N-HETEROARYLPIPERAZINYL UREAS AS MODULATORS OF FATTY ACID AMIDE HYDROLASE

(75) Inventors: Richard Apodaca, San Diego, CA (US); J. Guy Breitenbucher, Escondido, CA (US); Kanaka Pattabiraman, Palo Alto, CA (US); Mark Seierstad, San Diego, CA (US); Wei Xiao, San Diego, CA (US)

(73) Assignee: Janssen Pharmaceutica N.V. (BE)

( * ) Notice: Subject to any disclaimer, the term of this patent is extended or adjusted under 35 U.S.C. 154(b) by 97 days.

(21) Appl. No.: 11/478,128

(22) Filed: Jun. 28, 2006

(65) Prior Publication Data

US 2007/0004741 A1 Jan. 4, 2007

Related U.S. Application Data

(60) Provisional application No. 60/696,166, filed on Jun. 30, 2005.

(51) Int. Cl.
*A61K 31/496* (2006.01)
*A61K 31/505* (2006.01)
*A61K 31/5377* (2006.01)
*C07D 285/135* (2006.01)
*C07D 417/04* (2006.01)
*C07D 417/12* (2006.01)

(52) U.S. Cl. ............ 514/235.8; 514/227.8; 514/252.19; 514/253.11; 514/254.03; 544/58.2; 544/60; 544/121; 544/295; 544/364; 544/367

(58) Field of Classification Search ........................ None
See application file for complete search history.

(56) References Cited

U.S. PATENT DOCUMENTS

| | | | |
|---|---|---|---|
| 6,096,784 A | 8/2000 | Lerner et al. | |
| 6,462,054 B1 | 10/2002 | Boger | |
| 2004/0220191 A1 | 11/2004 | Schwink et al. | |
| 2005/0032747 A1* | 2/2005 | Bartolini et al. ............... | 514/80 |
| 2006/0089344 A1 | 4/2006 | Abouabdellah et al. | |
| 2006/0173184 A1 | 8/2006 | Apodaca et al. | |
| 2006/0293310 A1 | 12/2006 | Abouabdellah et al. | |
| 2007/0021403 A1 | 1/2007 | Abouabdellah et al. | |
| 2007/0021405 A1 | 1/2007 | Abouabdellah et al. | |
| 2007/0021424 A1 | 1/2007 | Abouabdellah et al. | |
| 2007/0027141 A1 | 2/2007 | Abouabdellah et al. | |
| 2008/0108629 A1* | 5/2008 | Kamboj et al. ......... | 514/254.03 |
| 2008/0139565 A1* | 6/2008 | Campbell et al. ............ | 514/243 |
| 2008/0312226 A1* | 12/2008 | Matsumoto et al. ...... | 514/233.8 |

FOREIGN PATENT DOCUMENTS

| | | |
|---|---|---|
| FR | 2854633 | 11/2004 |
| FR | 2864080 | 6/2005 |
| FR | 2865205 | 7/2005 |
| FR | 2866884 | 9/2005 |
| FR | 2866885 | 9/2005 |
| FR | 2866888 | 9/2005 |
| JP | 48010160 | 3/1973 |
| JP | 11139969 | 5/1999 |
| WO | WO 96/09817 | 4/1996 |
| WO | WO 96/21648 | 7/1996 |
| WO | WO 97/49667 | 12/1997 |
| WO | WO 98/37077 | 8/1998 |
| WO | WO 99/42107 | 8/1999 |
| WO | WO 02/08221 | 1/2002 |
| WO | WO 2004/033652 | 4/2004 |
| WO | WO 2006/054652 | 5/2006 |
| WO | WO 2006/085108 | 8/2006 |
| WO | WO 2006/088075 | 8/2006 |

OTHER PUBLICATIONS

Testa et al. Pure Appl. Chem. vol. 76, p. 907-914 (2004).*
Matsumoto et al. Chemical Abstracts, vol. 145, No. 8189 (abstract for WO 2006054652, May 26, 2006) (2006).*
Fox et al. Expert Opin.Investig.Drugs, vol. 14, p. 695-703 (2005).*
Teare et al. Expert Opin.Investig.Drugs, vol. 14, p. 859-869 (2005).*
Cravatt et al. Current Opinion in Chemical Biology, vol. 7, p. 469-475 (2003).*
Baker et al., "Cannabinoids controls spasticity and tremor in a multiple sclerosis model," *Nature* 2000, 404, 84-87.
Baker et al., "Endocannabinoids control spasticity in a multiple sclerosis model," *FASEB J.* 2001, 15(2), 300-302.
Boger et al., "Trifluoromethyl ketone inhibitors of fatty acid amide hydrolase: A probe of structural and conformational features contributing to inhibition," *Bioorg. Med. Chem. Lett.* 1999, 9, 265-270.

(Continued)

*Primary Examiner*—Emily Bernhardt
(74) *Attorney, Agent, or Firm*—Michael J. Atkins

(57) ABSTRACT

Certain N-heteroarylpiperazinyl urea compounds of Formula (I), as defined in the specification, are described, which are useful as FAAH inhibitors. Such compounds may be used in pharmaceutical compositions and methods for the treatment of disease states, disorders, and conditions mediated by fatty acid amide hydrolase (FAAH) activity. Thus, the compounds may be administered to treat, e.g., anxiety, pain, inflammation, sleep disorders, eating disorders, or movement disorders (such as multiple sclerosis).

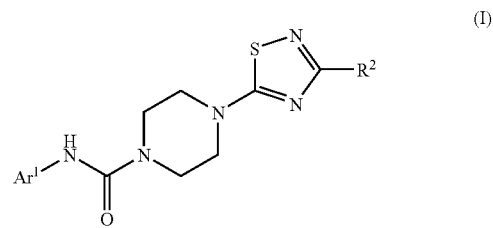

21 Claims, No Drawings

OTHER PUBLICATIONS

Boger et al., "Exceptionally potent inhibitors of fatty acid amide hydrolase: The enzyme responsible for degradation of endogenous oleamide and anandamide," *Proc. Natl. Acad. Sci.* USA 2000, 97(10), 5044-5049.

Boger et al., "α-Keto heterocycle inhibitors of fatty acid amide hydrolase: Carbonyl group modification and α-substitution," *Bioorg. Med. Chem. Lett.* 2001, 11, 1517-1520.

Cravatt et al., "Chemical characterization of a family of brain lipids that induce sleep," *Science* 1995, 268(5216), 1506-1509.

Cravatt et al., "Molecular characterization of an enzyme that degrades neuromodulatory fatty-acid amides," *Nature* 1996, 384(6604), 83-86.

Cravatt et al., "Supersensitivity to anandamide and enhanced endogenous cannabinoid signaling in mice lacking fatty acid amide hydrolase," *Proc. Natl. Acad. Sci.* USA 2001, 98(16), 9371-9376.

Devane et al., "Isolation and structure of a brain constituent that binds to the cannabinoid receptor," *Science* 1992, 258(5090), 1946-1949.

Goya et al., "Recent advances in cannabinoid receptor agonists and antagonists," *Exp. Opin. Ther. Patents* 2000, 10(10), 1529-1538.

Kathuria et al., "Modulation of anxiety through blockade of anandamide hydrolysis," *Nat. Med.* 2003, 9(1), 76-81.

Kirkham et al., "Endocannabinoid levels in rat limbic forebrain and hypothalamus in relation to fasting, feeding and satiation: stimulation of feeding by 2-arachidonyl glycerol," *Br. J. Pharmacol.* 2002, 136, 550-557.

Lambert et al., "The Palmitoylethanolamide and Oleamide Engmas: Are These Two Fatty Acid Amides Cannabimimetic?" *Curr. Med. Chem.* 1999, 6, 757-773.

Lambert et al., "The palmitoylethanolamide family: A new class of anti-inflammatory agents?" *Curr. Med. Chem.* 2002, 9(6), 663-674.

Mendelson et al., "The hypnotic actions of the fatty acid amide, oleamide," *Neuropsychopharmacology* 2001, 25(S5), S36-S39.

Piomelli, "The molecular logic of endocannabinoid signalling," *Nat. Rev. Neurosci.* 2003, 4(11), 873-884.

Robson, "Therapeutic aspects of cannabis and cannabinoids," *Br. J. Psychiatry* 2001, 178, 107-115.

Rodriguez de Fonseca et al., "An anorexic lipid mediator regulated by feeding," *Nature* 2001, 414, 209-212.

Svendsen et al., "Does the cannabinoid dronabinol reduce central pain in multiple sclerosis? Randomised double blind placebo controlled crossover trial," *Br. Med. J.* 2004, 329(7460), 253-260.

Ueda et al., "Purification and characterization of an acid amidase selective for N-palmitoylethanolamine, a putative endogenous anti-inflammatory substance," *J. Biol. Chem.* 2001, 276(38), 35552-35557.

CAS No. 681136-29-8, Catalog No. HAN 00375, 2005.

CAS No. 681136-27-6, Catalog No. HAN00373, 2005.

CAS No. 681136-26-5, Catalog No. HAN00372, 2005.

* cited by examiner

N-HETEROARYLPIPERAZINYL UREAS AS MODULATORS OF FATTY ACID AMIDE HYDROLASE

This application claims priority to U.S. Provisional Application No. 60/696,166, filed 30 Jun. 2005.

FIELD OF THE INVENTION

The present invention relates to certain N-heteroarylpiperazinyl urea compounds, pharmaceutical compositions containing them, and methods of using them for the treatment of disease states, disorders, and conditions mediated by fatty acid amide hydrolase (FAAH) activity.

BACKGROUND OF THE INVENTION

Medicinal benefits have been attributed to the cannabis plant for centuries. The primary bioactive constituent of cannabis is $\Delta_9$-tetrahydro-cannabinol (THC). The discovery of THC eventually led to the identification of two endogenous cannabinoid receptors responsible for its pharmacological actions, namely $CB_1$ and $CB_2$ (Goya, *Exp. Opin. Ther. Patents* 2000, 10, 1529). These discoveries not only established the site of action of THC, but also inspired inquiries into the endogenous agonists of these receptors, or "endocannabinoids". The first endocannabinoid identified was the fatty acid amide anandamide (AEA). AEA itself elicits many of the pharmacological effects of exogenous cannabinoids (Piomelli, *Nat. Rev. Neurosci.* 2003, 4(11), 873).

The catabolism of AEA is primarily attributable to the integral membrane bound protein fatty acid amide hydrolase (FAAH), which hydrolyzes AEA to arachidonic acid. FAAH was characterized in 1996 by Cravatt and co-workers (Cravatt, *Nature* 1996, 384, 83). It was subsequently determined that FAAH is additionally responsible for the catabolism of a large number of important lipid signaling fatty acid amides including: another major endocannabinoid, 2-arachidonoylglycerol (2-AG) (*Science* 1992, 258, 1946-1949); the sleep-inducing substance, oleamide (OEA) (*Science* 1995, 268, 1506); the appetite-suppressing agent, N-oleoylethanolamine (Rodriguez de Fonesca, *Nature* 2001, 414, 209); and the anti-inflammatory agent, palmitoylethanolamide (PEA) (Lambert, *Curr. Med. Chem.* 2002, 9(6), 663).

Small-molecule inhibitors of FAAH should elevate the concentrations of these endogenous signaling lipids and thereby produce their associated beneficial pharmacological effects. There have been some reports of the effects of various FAAH inhibitors in pre-clinical models.

Two carbamate-based inhibitors of FAAH were reported to have analgesic properties in animal models. In rats, BMS-1 (see WO 02/087569), which has the structure shown below, was reported to have an analgesic effect in the Chung spinal nerve ligation model of neuropathic pain, and the Hargraves test of acute thermal nociception. URB-597 was reported to have efficacy in the zero plus maze model of anxiety in rats, as well as analgesic efficacy in the rat hot plate and formalin tests (Kathuria, *Nat. Med.* 2003, 9(1), 76). The sulfonylfluoride AM374 was also shown to significantly reduce spasticity in chronic relapsing experimental autoimmune encephalomyelitis (CREAE) mice, an animal model of multiple sclerosis (Baker, *FASEB J.* 2001, 15(2), 300).

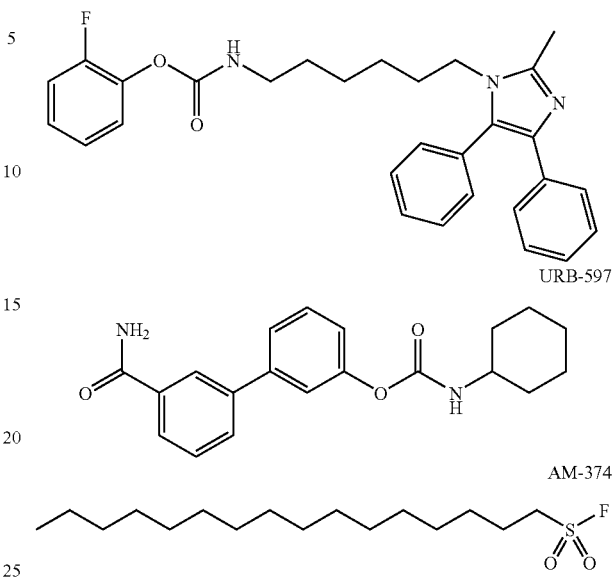

In addition, the oxazolopyridine ketone OL-135 is reported to be a potent inhibitor of FAAH, and has been reported to have analgesic activity in both the hot plate and tail emersion tests of thermal nociception in rats (WO 04/033652).

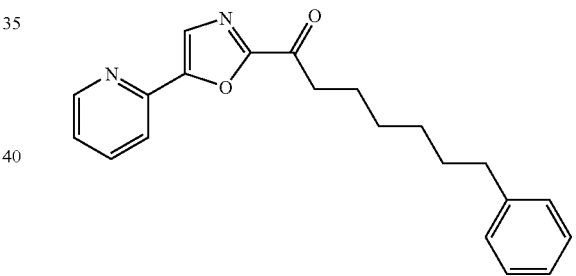

Results of research on the effects of certain exogenous cannabinoids has elucidated that a FAAH inhibitor may be useful for treating various conditions, diseases, disorders, or symptoms. These include pain, nausea/emesis, anorexia, spasticity, movement disorders, epilepsy and glaucoma. To date, approved therapeutic uses for cannabinoids include the relief of chemotherapy-induced nausea and emesis among patients with cancer and appetite enhancement in patients with HIV/AIDs who experience anorexia as a result of wasting syndrome. Two products are commercially available in some countries for these indications, namely, dronabinol (Marinol®) and nabilone.

Apart from the approved indications, a therapeutic field that has received much attention for cannabinoid use is analgesia, i.e., the treatment of pain. Five small randomized controlled trials showed that THC is superior to placebo, producing dose-related analgesia (Robson, *Br. J. Psychiatry* 2001, 178, 107-115). Atlantic Pharmaceuticals is developing a synthetic cannabinoid, CT-3, a 1,1-dimethyl heptyl derivative of the carboxylic metabolite of tetrahydrocannabinol, as an orally active analgesic and anti-inflammatory agent. A pilot phase II trial in chronic neuropathic pain was initiated with CT-3 in Germany in May 2002.

Many individuals with multiple sclerosis have claimed a benefit from cannabis for both disease-related pain and spasticity, with support from small controlled trials (Svendsen, *Br. Med. J.* 2004, 329, 253). Likewise, victims of spinal cord injuries, such as paraplegia, have reported for years that their painful spasms are alleviated after smoking marijuana. Recently, a report showing that cannabinoids appear to control spasticity and tremor in the CREAE model of multiple sclerosis demonstrated that these effects are mediated by $CB_1$ and $CB_2$ receptors (Baker, *Nature* 2000, 404, 84-87). Phase 3 clinical trials are currently underway in multiple sclerosis and spinal cord injury patients with a narrow ratio mixture of tetrahydrocannabinol/cannabidiol (THC/CBD).

Small-scale controlled trials have been conducted to investigate other potential commercial uses of cannabinoids. Trials in volunteers confirmed that oral, injected and smoked cannabinoids produced dose-related reductions in intraocular pressure (IOP) and therefore may relieve glaucoma symptoms. Ophthalmologists have prescribed cannabis for patients with glaucoma in whom other drugs have failed to adequately control intraocular pressure (Robson, 2001).

Inhibition of FAAH using a small-molecule inhibitor may be advantageous compared to treatment with a direct-acting $CB_1$ agonist. Administration of exogenous $CB_1$ agonists may produce a range of responses, including reduced nociception, catalepsy, hypothermia, and increased feeding behavior. These four in particular are termed the "cannabinoid tetrad." Experiments with FAAH −/− mice show reduced responses in tests of nociception, but did not show catalepsy, hypothermia, or increased feeding behavior (Cravatt, *Proc. Natl. Acad. Sci. USA* 2001, 98(16), 9371). Fasting caused levels of AEA to increase in rat limbic forebrain, but not in other brain areas, providing evidence that stimulation of AEA biosynthesis may be anatomically regionalized to targeted CNS pathways (Kirkham, *Br. J. Pharmacol.* 2002, 136, 550). The finding that AEA increases are localized within the brain, rather than systemic, suggests that FAAH inhibition with a small molecule could enhance the actions of AEA and other fatty acid amides in tissue regions where synthesis and release of these signaling molecules is occurring in a given pathophysiological condition (Piomelli, 2003).

In addition to the effects of a FAAH inhibitor on AEA and other endocannabinoids, inhibitors of FAAH's catabolism of other lipid mediators may be used in treating other therapeutic indications. For example, PEA has demonstrated biological effects in animal models of inflammation, immunosuppression, analgesia, and neuroprotection (Ueda, *J. Biol. Chem.* 2001, 276(38), 35552). Oleamide, another substrate of FAAH, induces sleep (Boger, *Proc. Natl. Acad. Sci. USA* 2000, 97(10), 5044; Mendelson, *Neuropsychopharmacology* 2001, 25, S36).

Thus, there is evidence that small-molecule FAAH inhibitors may be useful in treating pain of various etiologies, anxiety, multiple sclerosis and other movement disorders, nausea/emesis, eating disorders, epilepsy, glaucoma, inflammation, immunosuppression, neuroprotection, and sleep disorders, and potentially with fewer side effects than treatment with an exogenous cannabinoid. Various small-molecule FAAH modulators have been reported, e.g., in WO 04/033652, U.S. Pat. No. 6,462,054, U.S. Pat. No. 6,096,784, WO 99/26584, WO 97/49667, and WO 96/09817. There remains a need, however, for potent FMH modulators with desirable pharmaceutical properties.

Certain piperazinyl or piperidinyl derivatives have been disclosed in the literature for different uses. For example, JP 11139969 describes certain phenol derivatives as antioxidants and ACAT inhibitors; WO 96/21648 discloses various piperazine derivatives as antitumor agents; JP 48010160 describes certain piperazine derivatives as anti-inflammatory agents; WO 04/072025 discloses certain substituted N-aryl-heterocycles as obesity, diabetes, and drug abuse agents; DE 2123784 and U.S. Pat. No. 3,813,395 disclose various piperazinylthieno-benzothiazepines as psychotropics and anesthetics; and WO 98/37077 and WO 99/42107describe certain piperazine-based compounds as calcitonin mimetics for treatment of bone deficits. Additionally, WO 97/42230 describes a solid-phase synthesis of certain piperazine ureas. WO 97/23458 discloses certain piperidine derivatives as intermediates toward NMDA receptor ligands. 4-(3-Phenyl-[1,2,4] thiadiazol-5-yl)-piperazine-1-carboxylic acid phenylamide (CAS No. 681136-29-8) is commercially available from Maybridge.

SUMMARY OF THE INVENTION

Certain piperazinyl or piperidinyl derivatives have now been found to have FMH-modulating activity.

Thus, in one general aspect, the invention relates to compounds of the following Formula (I):

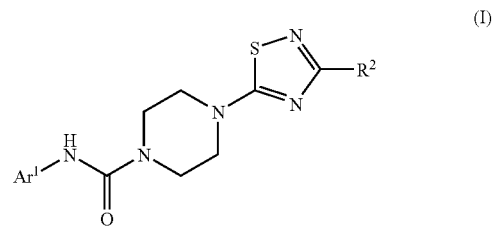

wherein:
Ar$^1$ is a pyridyl, pyrimidinyl, thiazolyl, oxazolyl, naphthyl, or phenyl group, unsubstituted or substituted at a carbon ring member with one or two R$^a$ moieties;
where each R$^a$ moiety is independently selected from the group consisting of —C$_{1-4}$alkyl, —C$_{3-7}$cycloalkyl, phenyl, benzyloxy, —C$_{2-4}$alkenyl, —NO$_2$, —CN, —OH, —OC$_{1-4}$alkyl, fluoro, chloro, bromo, iodo, —CF$_3$, —OCF$_3$, —SCF$_3$, —SH, —SC$_{1-4}$alkyl, —SO$_2$C$_{1-4}$alkyl, —SOC$_{1-4}$alkyl, —CO$_2$C$_{1-4}$alkyl, —CO$_2$H, —COC$_{1-4}$alkyl, —SO$_2$NR$^b$R$^c$, —NR$^b$SO$_2$R$^c$, —C(=O)NR$^b$R$^c$, —NR$^b$C(=O)R$^c$, and —N(R$^b$)R$^c$, where R$^b$ and R$^c$ are each independently —H or —C$_{1-4}$alkyl, or R$^b$ and R$^c$ are taken together to form a 4- to 7-membered heterocycloalkyl ring; and
R$^2$ is R$^3$, R$^4$, or Ar$^2$,
where R$^3$ is a —N-piperidinyl, —N-piperazinyl, —N-morpholinyl, —N-thiomorpholinyl, —N-dioxo-1λ$^6$-thiomorpholinyl, or —N-pyrrolidinyl group, unsubstituted or substituted with one or two R$^d$ moieties;
where each R$^d$ moiety is independently selected from the group consisting of —C$_{1-4}$alkyl, —C$_{3-7}$cycloalkyl, phenyl, —OH, and —C$_{2-4}$alkenyl;
R$^4$ is —NR$^e$R$^f$, wherein R$^e$ and R$^f$ are each independently —H, —C$_{1-4}$alkyl, or —C$_{3-7}$cycloalkyl; and
Ar$^2$ is a phenyl, thiophenyl, furanyl, pyridyl, pyrimidinyl, or pyrazinyl group, unsubstituted or substituted at a carbon ring member with one or two R$^g$ moieties;
where each R$^g$ moiety is independently selected from the group consisting of —C$_{1-4}$alkyl, —C$_{3-7}$cycloalkyl, phenyl, —C$_{2-4}$alkenyl, —NO$_2$, —CN, —OC$_{1-4}$alkyl, fluoro, chloro, bromo, iodo, —CF$_3$, —OCF$_3$, —SCF$_3$, —SC$_{1-4}$alkyl, —SO$_2$C$_{1-4}$alkyl, —SOC$_{1-4}$alkyl, —CO$_2$C$_{1-4}$alkyl, —COC$_{1-4}$alkyl, —SO$_2$NR$^h$R$^i$, —NR$^h$SO$_2$R$^i$, —C(=O)NR$^h$R$^i$, —NR$^b$C(=O)R$^c$, and —N(R$^h$)R$^i$, where R$^h$ and R$^i$ are each independently —H or —C$_{1-4}$alkyl, or R$^b$ and R$^c$ are taken together to form a 4- to 7-membered heterocycloalkyl ring; and further wherein Ar$^1$ and R$^2$ are not both unsubstituted phenyl;

or a pharmaceutically acceptable salt, pharmaceutically acceptable prodrug, or pharmaceutically active metabolite of such compound.

In preferred embodiments, the compound of Formula (I) is a compound specifically described or exemplified in the detailed description below.

In a further general aspect, the invention relates to pharmaceutical compositions each comprising: (a) an effective amount of an agent selected from compounds of Formula (I) and pharmaceutically acceptable salts, pharmaceutically acceptable prodrugs, and pharmaceutically active metabolites thereof; and (b) a pharmaceutically acceptable excipient.

In another general aspect, the invention is directed to a method of treating a subject suffering from or diagnosed with a disease, disorder, or medical condition mediated by FAAH activity, comprising administering to the subject in need of such treatment an effective amount of a compound of Formula (I) wherein:

Ar$^1$ is a pyridyl, pyrimidinyl, thiazolyl, oxazolyl, naphthyl, or phenyl group, unsubstituted or substituted at a carbon ring member with one or two R$^a$ moieties;

where each R$^a$ moiety is independently selected from the group consisting of —C$_{1-4}$alkyl, —C$_{3-7}$cycloalkyl, phenyl, benzyloxy, —C$_{2-4}$alkenyl, —NO$_2$, —CN, —OH, —OC$_{1-4}$alkyl, fluoro, chloro, bromo, iodo, —CF$_3$, —OCF$_3$, —SCF$_3$, —SH, —SC$_{1-4}$alkyl, —SO$_2$C$_{1-4}$alkyl, —SOC$_{1-4}$alkyl, —CO$_2$C$_{1-4}$alkyl, —CO$_2$H, —COC$_{1-4}$alkyl, —SO$_2$NR$^b$R$^c$, —NR$^b$SO$_2$R$^c$, —C(=O)NR$^b$R$^c$, —NR$^b$C(=O)R$^c$, and —N(R$^b$)R$^c$, where R$^b$ and R$^c$ are each independently —H or —C$_{1-4}$alkyl, or R$^b$ and R$^c$ are taken together to form a 4- to 7-membered heterocycloalkyl ring; and R$^2$ is R$^3$, R$^4$, or Ar$^2$, where R$^3$ is a —N-piperidinyl, —N-piperazinyl, —N-morpholinyl, —N-thiomorpholinyl, —N-dioxo-1λ$^6$-thiomorpholinyl, or —N-pyrrolidinyl group, unsubstituted or substituted with one or two R$^d$ moieties;

where each R$^d$ moiety is independently selected from the group consisting of —C$_{1-4}$alkyl, —C$_{3-7}$cycloalkyl, phenyl, —OH, and —C$_{2-4}$alkenyl;

R$^4$ is —NR$^e$R$^f$, wherein R$^e$ and R$^f$ are each independently —H, —C$_{1-4}$alkyl, or —C$_{3-7}$cycloalkyl; and Ar$^2$ is a phenyl, thiophenyl, furanyl, pyridyl, pyrimidinyl, or pyrazinyl group, unsubstituted or substituted at a carbon ring member with one or two R$^g$ moieties;

where each R$^g$ moiety is independently selected from the group consisting of —C$_{1-4}$alkyl, —C$_{3-7}$cycloalkyl, phenyl, —C$_{2-4}$alkenyl, —NO$_2$, —CN, —OC$_{1-4}$alkyl, fluoro, chloro, bromo, iodo, —CF$_3$, —OCF$_3$, —SCF$_3$, —SC$_{1-4}$alkyl, —SO$_2$C$_{1-4}$alkyl, —SOC$_{1-4}$alkyl, —CO$_2$C$_{1-4}$alkyl, —COC$_{1-4}$alkyl, —SO$_2$NR$^h$R$^i$, —NR$^h$SO$_2$R$^i$, —C(=O)NR$^h$R$^i$, —NR$^b$C(=O)R$^c$, and —N(R$^h$)R$^i$, where R$^h$ and R$^i$ are each independently —H or —C$_{1-4}$alkyl, or R$^b$ and R$^c$ are taken together to form a 4- to 7-membered heterocycloalkyl ring;

or a pharmaceutically acceptable salt, pharmaceutically acceptable prodrug, or pharmaceutically active metabolite of such compound.

In certain preferred embodiments of the inventive method, the disease, disorder, or medical condition is selected from: anxiety, pain, sleep disorders, eating disorders, inflammation, multiple sclerosis and other movement disorders, HIV wasting syndrome, closed head injury, stroke, Alzheimer's disease, epilepsy, Tourette's syndrome, Niemann-Pick disease, Parkinson's disease, Huntington's chorea, optic neuritis, autoimmune uveitis, symptoms of drug withdrawal, nausea, emesis, sexual dysfunction, post-traumatic stress disorder, cerebral vasospasm, glaucoma, irritable bowel syndrome, inflammatory bowel disease, immunosuppression, gastroesophageal reflux disease, paralytic ileus, secretory diarrhea, gastric ulcer, rheumatoid arthritis, unwanted pregnancy, hypertension, cancer, hepatitis, allergic airway disease, autoimmune diabetes, intractable pruritis, and neuroinflammation.

Additional embodiments, features, and advantages of the invention will be apparent from the appended claims, which are incorporated into this summary by reference, as well as from the following detailed description.

DETAILED DESCRIPTION OF INVENTION AND ITS PREFERRED EMBODIMENTS

The invention may be more fully appreciated by reference to the following description, including the following glossary of terms and the concluding examples. For the sake of brevity, the disclosures of the publications cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Exemplary alkyl groups include methyl (Me, which also may be structurally depicted by /), ethyl (Et), n-propyl, isopropyl, butyl, isobutyl, sec-butyl, tert-butyl (tBu), pentyl, isopentyl, tert-pentyl, hexyl, isohexyl, and the like.

The term "alkylene" refers to a divalent straight- or branched-chain alkyl group having from 1 to 12 carbon atoms in the chain. Exemplary alkylene groups include methylene, ethylene, propylene, and the like.

The term "alkenyl" refers to a straight- or branched-chain alkenyl group having from 2 to 12 carbon atoms in the chain. (The double bond of the alkenyl group is formed by two sp$^2$ hybridized carbon atoms.) Illustrative alkenyl groups include prop-2-enyl, but-2-enyl, but-3-enyl, 2-methylprop-2-enyl, hex-2-enyl, and the like.

The term "alkynyl" refers to a straight- or branched-chain alkynyl group having from 2 to 12 carbon atoms in the chain. (The triple bond of the alkynyl group is formed by two sp hybridized carbon atoms.) Illustrative alkynyl groups include prop-2-ynyl, but-2-ynyl, but-3-ynyl, 2-methylbut-2-ynyl, hex-2-ynyl, and the like.

The term "aryl" refers to a monocyclic, or fused or spiro polycyclic, aromatic carbocycle (ring structure having ring atoms that are all carbon) having from 3 to 12 ring atoms per ring. (Carbon atoms in aryl groups are sp$^2$ hybridized.) Illustrative examples of aryl groups include the following moieties:

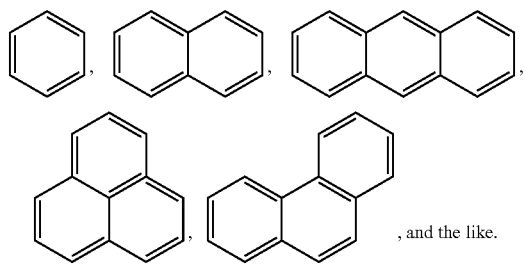

The term "heteroaryl" refers to a monocyclic, or fused or spiro bicyclic or polycyclic, aromatic heterocycle (ring structure having ring atoms selected from carbon atoms as well as nitrogen, oxygen, and sulfur heteroatoms) having from 3 to 12 ring atoms per ring. Illustrative examples of aryl groups include the following moieties:

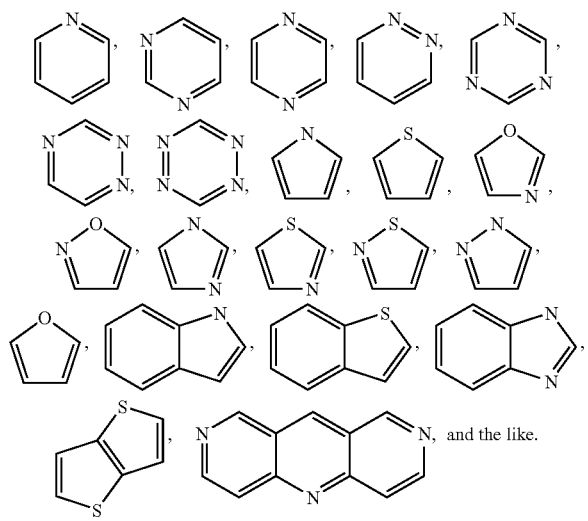

The term "cycloalkyl" refers to a saturated or partially saturated, monocyclic or fused or spiro polycyclic, carbocycle having from 3 to 12 ring atoms per ring. Illustrative examples of cycloalkyl groups include the following moieties:

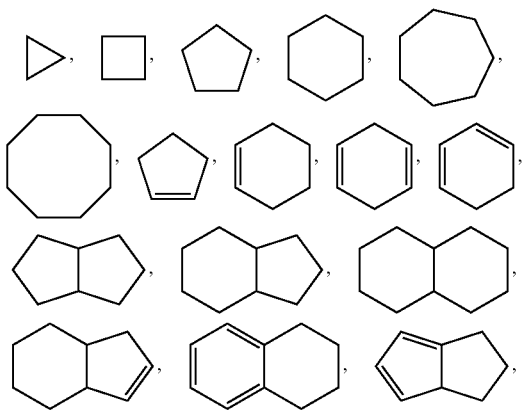

-continued

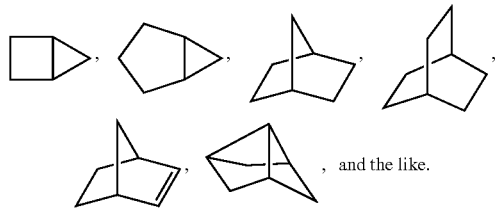

A "heterocycloalkyl" refers to a monocyclic, or fused or spiro polycyclic, ring structure that is saturated or partially saturated and has from 3 to 12 ring atoms per ring selected from C atoms and N, O, and S heteroatoms. Illustrative examples of heterocycloalkyl groups include:

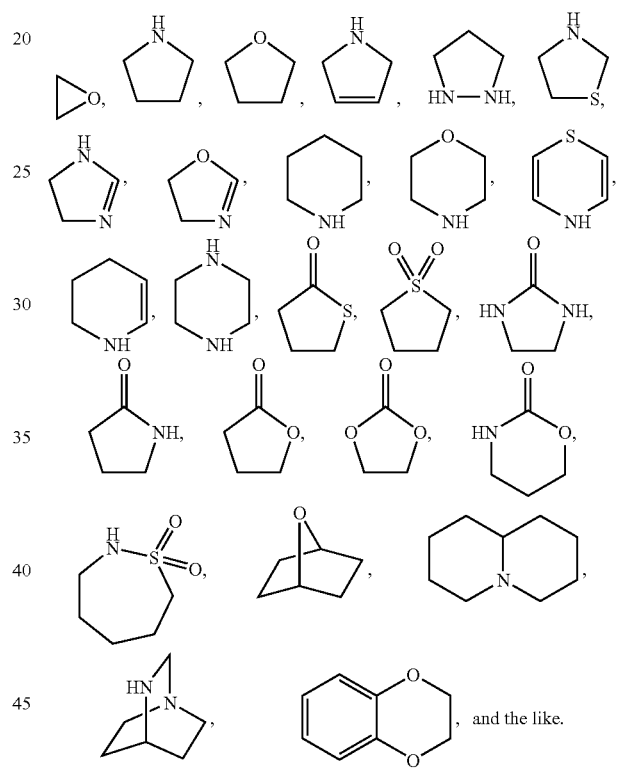

The term "halogen" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

Formula (I) is intended to represent compounds having structures depicted by the structural formula as well as certain variations or forms. In particular, compounds of Formula (I) may have asymmetric centers and therefore exist in different enantiomeric forms. All optical isomers and stereoisomers of the compounds of the general formula, and mixtures thereof, are considered within the scope of the formula. Thus Formula (I) is intended to represent a racemate, one or more enantiomeric forms, one or more diastereomeric forms, one or more atropisomeric forms, and mixtures thereof.

Furthermore, certain structures depicted by Formula (I) may exist as geometric isomers (i.e., cis and trans isomers), as tautomers, or as atropisomers. Additionally, Formula (I) is intended to represent hydrates, solvates, and polymorphs of such compounds, and mixtures thereof.

Formula (I) is also intended to represent unlabeled forms as well as isotopically labeled forms of the compounds. Isotopically labeled compounds have structures depicted by Formula (I) except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Various isotopically labeled compounds of the present invention, for example those into which radioactive isotopes such as $^3H$, $^{11}C$, and $^{14}C$ are incorporated, are useful in drug or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to Formula (I), the selection of a particular moiety from a list of possible species for a specified variable is not intended to define the moiety for the variable appearing elsewhere. In other words, where a variable appears more than once, the choice of the species from a specified list is independent of the choice of the species for the same variable elsewhere in the formula.

In preferred embodiments of the invention, $Ar^1$ is a phenyl, 2-naphthyl, 2-pyridyl, 3-pyridyl, 4-pyridyl, 2-pyrimidinyl, or 2-thiazolyl group, unsubstituted or substituted at a carbon ring atom with one or two $R^a$ moieties. In further preferred embodiments, $Ar^1$ is a phenyl group unsubstituted or substituted at a carbon ring atom with one or two $R^a$ moieties. Preferably, $Ar^1$ is 2-chlorophenyl, 3-fluorophenyl, 4-fluorophenyl, 4-methoxyphenyl, 4-benzyloxyphenyl, 3-methylphenyl, 2-nitrophenyl, 2-methoxyphenyl, 3-chlorophenyl, 4-methylphenyl, 2-methylphenyl, 3-methoxyphenyl, 2-methylsulfanylphenyl, 4-biphenyl, 4-ethoxyphenyl, 2-fluorophenyl, 4-chlorophenyl, 2-isopropylphenyl, 2-trifluoromethyl, 4-nitrophenyl, 4-dimethylaminophenyl, 4-carbomethoxyphenyl, naphthyl, 2-pyridyl, 3-pyridyl, 4-pyridyl, 2-pyrimidinyl, 2-naphthyl, 2-thiazolyl, or (unsubstituted) phenyl. More preferably, $Ar^1$ is a phenyl group unsubstituted or substituted with fluoro or chloro. Even more preferably, $Ar^1$ is 2-pyrimidinyl, 2-thiazolyl, 2-pyridyl, 3-pyridyl, or 4-pyridyl.

In preferred embodiments, $R^2$ is a —N-piperidinyl, —N-piperazinyl, —N-morpholinyl, or N-pyrrolidinyl group, unsubstituted or substituted at a carbon ring atom with one or two $R^d$ moieties. More preferably, $R^2$ is —N-piperidinyl, 4-methyl-N-piperidinyl, —N-piperazinyl, —N-morpholinyl, or N-pyrrolidinyl. Alternatively, $R^2$ is a phenyl, 3-furanyl, thiophen-2-yl, or thiophen-3-yl group, unsubstituted or substituted at a carbon ring atom with one or two $R^g$ moieties.

Preferably, $R^2$ is —N-piperidinyl, 4-methyl-N-piperidinyl, —N-piperazinyl, —N-morpholinyl, —N-pyrrolidinyl, 4-methylphenyl, 4-methoxyphenyl, 4-chlorophenyl, 4-fluorophenyl, 3,5-dichlorophenyl, 3-nitrophenyl, 3-methylphenyl, 3-furanyl, thiophen-2-yl, thiophen-3-yl, or (unsubstituted) phenyl. More preferably, $R^2$ is a phenyl group, unsubstituted or mono- or di-substituted with fluoro or chloro, 2-furanyl, 3-furanyl, thiophen-2-yl, or thiophen-3-yl.

Preferred compounds of the present invention include the following:

- 4-(3-phenyl-[1,2,4]thiadiazol-5-yl)-piperazine-1-carboxylic acid phenylamide;
- 4-(3-phenyl-[1,2,4]thiadiazol-5-yl)-piperazine-1-carboxylic acid (2-chloro-phenyl)-amide;
- 4-(3-phenyl-[1,2,4]thiadiazol-5-yl)-piperazine-1-carboxylic acid (3-fluoro-phenyl)-amide;
- 4-(3-phenyl-[1,2,4]thiadiazol-5-yl)-piperazine-1-carboxylic acid (4-fluoro-phenyl)-amide;
- 4-(3-phenyl-[1,2,4]thiadiazol-5-yl)-piperazine-1-carboxylic acid (4-methoxy-phenyl)-amide;
- 4-(3-phenyl-[1,2,4]thiadiazol-5-yl)-piperazine-1-carboxylic acid (4-benzyloxy-phenyl)-amide;
- 4-(3-phenyl-[1,2,4]thiadiazol-5-yl)-piperazine-1-carboxylic acid m-tolylamide;
- 4-(3-phenyl-[1,2,4]thiadiazol-5-yl)-piperazine-1-carboxylic acid (2-nitro-phenyl)-amide;
- 4-(3-phenyl-[1,2,4]thiadiazol-5-yl)-piperazine-1-carboxylic acid (2-methoxy-phenyl)-amide;
- 4-(3-phenyl-[1,2,4]thiadiazol-5-yl)-piperazine-1-carboxylic acid (3-chloro-phenyl)-amide;
- 4-(3-phenyl-[1,2,4]thiadiazol-5-yl)-piperazine-1-carboxylic acid p-tolylamide;
- 4-(3-phenyl-[1,2,4]thiadiazol-5-yl)-piperazine-1-carboxylic acid o-tolylamide;
- 4-(3-phenyl-[1,2,4]thiadiazol-5-yl)-piperazine-1-carboxylic acid (2-methylsulfanyl-phenyl)-amide;
- 4-(3-phenyl-[1,2,4]thiadiazol-5-yl)-piperazine-1-carboxylic acid (3-methoxy-phenyl)-amide;
- 4-(3-phenyl-[1,2,4]thiadiazol-5-yl)-piperazine-1-carboxylic acid biphenyl-4-ylamide;
- 4-(3-phenyl-[1,2,4]thiadiazol-5-yl)-piperazine-1-carboxylic acid naphthalen-2-ylamide;
- 4-(3-phenyl-[1,2,4]thiadiazol-5-yl)-piperazine-1-carboxylic acid (4-ethoxy-phenyl)-amide;
- 4-(3-p-tolyl-[1,2,4]thiadiazol-5-yl)-piperazine-1-carboxylic acid phenylamide;
- 4-[3-(4-methoxy-phenyl)-[1,2,4]thiadiazol-5-yl]-piperazine-1-carboxylic acid phenylamide;
- 4-[3-(4-chloro-phenyl)-[1,2,4]thiadiazol-5-yl]-piperazine-1-carboxylic acid phenylamide;
- 4-(3-phenyl-[1,2,4]thiadiazol-5-yl)-piperazine-1-carboxylic acid (2-fluoro-phenyl)-amide;
- 4-(3-phenyl-[1,2,4]thiadiazol-5-yl)-piperazine-1-carboxylic acid (4-chloro-phenyl)-amide;
- 4-(3-phenyl-[1,2,4]thiadiazol-5-yl)-piperazine-1-carboxylic acid (2-isopropyl-phenyl)-amide;
- 4-(3-phenyl-[1,2,4]thiadiazol-5-yl)-piperazine-1-carboxylic acid (2-trifluoromethyl-phenyl)-amide;
- 4-(3-phenyl-[1,2,4]thiadiazol-5-yl)-piperazine-1-carboxylic acid (4-nitro-phenyl)-amide;
- 4-(3-phenyl-[1,2,4]thiadiazol-5-yl)-piperazine-1-carboxylic acid (4-dimethylamino-phenyl)-amide;
- 4-(3-piperidin-1-yl-[1,2,4]thiadiazol-5-yl)-piperazine-1-carboxylic acid phenylamide;
- 4-(3-pyrrolidin-1-yl-[1,2,4]thiadiazol-5-yl)-piperazine-1-carboxylic acid phenylamide;

4-[3-(4-methyl-piperidin-1-yl)-[1,2,4]thiadiazol-5-yl]-piperazine-1-carboxylic acid phenylamide;
4-{[4-(3-phenyl-[1,2,4]thiadiazol-5-yl)-piperazine-1-carbonyl]-amino}-benzoic acid methyl ester;
4-(3-phenyl-[1,2,4]thiadiazol-5-yl)-piperazine-1-carboxylic acid pyrimidin-2-ylamide;
4-(3-phenyl-[1,2,4]thiadiazol-5-yl)-piperazine-1-carboxylic acid thiazol-2-ylamide;
4-(3-phenyl-[1,2,4]thiadiazol-5-yl)-piperazine-1-carboxylic acid pyridin-4-ylamide;
4-(3-phenyl-[1,2,4]thiadiazol-5-yl)-piperazine-1-carboxylic acid pyridin-2-ylamide;
4-(3-phenyl-[1,2,4]thiadiazol-5-yl)-piperazine-1-carboxylic acid pyridin-3-ylamide;
4-[3-(4-fluoro-phenyl)-[1,2,4]thiadiazol-5-yl]-piperazine-1-carboxylic acid phenylamide;
4-[3-(3-nitro-phenyl)-[1,2,4]thiadiazol-5-yl]-piperazine-1-carboxylic acid phenylamide;
4-(3-m-tolyl-[1,2,4]thiadiazol-5-yl)-piperazine-1-carboxylic acid phenylamide;
4-[3-(3,5-dichloro-phenyl)-[1,2,4]thiadiazol-5-yl]-piperazine-1-carboxylic acid phenylamide;
4-(3-furan-2-yl-[1,2,4]thiadiazol-5-yl)-piperazine-1-carboxylic acid phenylamide;
4-(3-furan-3-yl-[1,2,4]thiadiazol-5-yl)-piperazine-1-carboxylic acid phenylamide;
4-(3-thiophen-2-yl-[1,2,4]thiadiazol-5-yl)-piperazine-1-carboxylic acid phenylamide;
4-(3-thiophen-3-yl-[1,2,4]thiadiazol-5-yl)-piperazine-1-carboxylic acid phenylamide; and
4-(3-morpholin-4-yl-[1,2,4]thiadiazol-5-yl)-piperazine-1-carboxylic acid phenylamide;

and pharmaceutically acceptable salts thereof.

The invention includes also pharmaceutically acceptable salts of the compounds represented by Formula (I). Pharmaceutically acceptable salts of the above-described specific compounds are especially preferred.

A "pharmaceutically acceptable salt" is intended to mean a salt of a free acid or base of a compound represented by Formula (I) that is not toxic, biologically intolerable, or otherwise biologically undesirable. Preferred pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt. Exemplary pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the compound of Formula (I) is a base, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid or ethanesulfonic acid, or the like.

If the compound of Formula (I) is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine and piperazine, and inorganic salts derived from sodium, calcium, potassium, magnesium, manganese, iron, copper, zinc, aluminum and lithium.

The invention also relates to treatment methods employing pharmaceutically acceptable prodrugs of the compounds of Formula (I). The term "prodrug" means a precursor of a designated compound that, following administration to a subject, yields the compound in vivo via a chemical or physiological process such as solvolysis or physiological conditions (e.g., a prodrug on being brought to physiological pH is converted to the compound of Formula (I)). A "pharmaceutically acceptable prodrug" is a prodrug that is not toxic, biologically intolerable, or otherwise biologically unsuitable for administration to the subject.

Exemplary prodrugs include compounds having an amino acid residue, or a polypeptide chain of two or more (e.g., two, three or four) amino acid residues, covalently joined through an amide or ester bond to a free amino, hydroxy or carboxylic acid group of a compound of Formula (I). Examples of amino acid residues include the twenty naturally occurring amino acids commonly designated by three letter symbols as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Exemplary amides include those derived from ammonia, primary $C_{1-6}$alkyl amines and secondary di($C_{1-6}$alkyl) amines. Secondary amines include 5- or 6-membered heterocycloalkyl or heteroaryl ring moieties having from 1 to 3 heteroatoms where at least one is a nitrogen atom. Preferred amides are derived from ammonia, $C_{1-3}$alkyl primary amines, and di($C_{1-2}$alkyl) amines. Exemplary esters of the invention include $C_{1-7}$alkyl, $C_{5-7}$carbocyclyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in *Adv. Drug Delivery Rev.* 1996, 19, 115. Carbamate derivatives of hydroxy and amino groups may also yield prodrugs. Carbonate derivatives, sulfonate esters and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine or carboxylic acid functionalities, or where the acyl group is an amino acid ester as described above, is also useful to yield prodrugs. Prodrugs of this type may be prepared as described in *J. Med. Chem.* 1996, 39, 10. Free amines can also be derivatized as amides, sulfonamides or phosphonamides. All of these prodrug moieties may incorporate groups including ether, amine and carboxylic acid functionalities.

Pharmaceutically active metabolites may also be used in the methods of the invention. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 224-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

The compounds of Formula (I) and their pharmaceutically acceptable salts, pharmaceutically acceptable prodrugs, and pharmaceutically active metabolites (collectively, "agents") of the present invention are useful as FAAH inhibitors in the methods of the invention. The agents may be used in the inventive methods for the treatment or prevention of medical conditions, diseases, or disorders mediated through inhibition or modulation of FAAH, such as those described herein. Agents according to the invention may therefore be used as an analgesic, neuroprotectant, sedative, appetite stimulant, or contraceptive.

Exemplary medical conditions, diseases, and disorders include anxiety, pain, sleep disorders, eating disorders, inflammation, multiple sclerosis and other movement disorders, HIV wasting syndrome, closed head injury, stroke, Alzheimer's disease, epilepsy, Tourette's syndrome, epilepsy, Niemann-Pick disease, Parkinson's disease, Huntington's chorea, optic neuritis, autoimmune uveitis, symptoms of drug withdrawal, nausea, emesis, sexual dysfunction, post-traumatic stress disorder, or cerebral vasospasm.

Thus, the pharmaceutical agents may be used to treat subjects diagnosed with or suffering from a disorder or condition mediated through FMH activity. The term "treat" or "treating" as used herein is intended to refer to administration of an agent or composition of the invention to a subject for the purpose of effecting a therapeutic or prophylactic benefit through modulation of FAAH activity. Treating includes reversing, ameliorating, alleviating, inhibiting the progress of, lessening the severity of, or preventing a disease, disorder or condition, or one or more symptoms of such disease, disorder or condition mediated through modulation of FAAH activity. The term "subject" refers to a mammalian patient in need of such treatment, such as a human. "Modulators" include both inhibitors and activators, where "inhibitors" refer to compounds that decrease, prevent, inactivate, desensitize or down-regulate FAAH expression or activity, and "activators" are compounds that increase, activate, facilitate, sensitize or up-regulate FAAH expression or activity.

Accordingly, the invention relates to methods of using the pharmaceutical agents described herein to treat subjects diagnosed with or suffering from a disorder or condition mediated through FAAH activity, such as: anxiety, pain, sleep disorders, eating disorders, inflammation, or movement disorders (e.g., multiple sclerosis).

Symptoms or disease states are intended to be included within the scope of "medical conditions, disorders, or diseases." For example, pain may be associated with various diseases and disorders, and may include various etiologies. Illustrative types of pain treatable with a FAAH-modulating agent according to the invention include cancer pain, postoperative pain, GI tract pain, spinal cord injury pain, visceral hyperalgesia, thalamic pain, headache (including stress headache and migraine), low back pain, neck pain, musculoskeletal pain, peripheral neuropathic pain, central neuropathic pain, neurogenerative disorder related pain, and menstrual pain. HIV wasting syndrome includes associated symptoms such as appetite loss and nausea. Parkinson's disease includes, for example, levodopa-induced dyskinesia. Treatment of multiple sclerosis may include treatment of symptoms such as spasticity, neurogenic pain, central pain, or bladder dysfunction. Symptoms of drug withdrawal may be caused by, for example, addiction to opiates or nicotine. Nausea or emesis may be due to chemotherapy, postoperative, or opioid related causes. Treatment of sexual dysfunction may include improving libido or delaying ejaculation. Treatment of cancer may include treatment of glioma. Sleep disorders include, for example, sleep apnea, insomnia, and disorders calling for treatment with an agent having a sedative or narcotic-type effect. Eating disorders include, for example, anorexia or appetite loss associated with a disease such as cancer or HIV infection/AIDS.

In a treatment method according to the invention, an effective amount of a pharmaceutical agent according to the invention is administered to a subject suffering from or diagnosed as having such a disease, disorder or condition. An "effective amount" means an amount or dose sufficient to generally bring about the desired therapeutic or prophylactic benefit in patients in need of such treatment.

Effective amounts or doses of the agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disorder or condition, the subject's previous or ongoing therapy, the subject's health status and response to drugs, and the judgment of the treating physician. An exemplary dose is in the range of from about 0.001 to about 200 mg of agent per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's conditions has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the agents of the invention may be used in combination with additional active compounds in the treatment of the above conditions. The additional compounds may be coadministered separately with an agent of Formula (I) or included with such an agent as an additional active ingredient in a pharmaceutical composition according to the invention. In an exemplary embodiment, additional active compounds are those that are known or discovered to be effective in the treatment of conditions, disorders, or diseases mediated by FAAH activity, such as another FAAH modulator or a compound active against another target associated with the particular condition, disorder, or disease. The combination may serve to increase efficacy (e.g., by including in the combination a compound potentiating the potency or effectiveness of an agent according to the invention), decrease one or more side effects, or decrease the required dose of the agent according to the invention. In one illustrative embodiment, a composition according to the invention may contain one or more additional active ingredients selected from opioids, NSAIDs (e.g., ibuprofen, cyclooxygenase-2 (COX-2) inhibitors, and naproxen), gabapentin, pregabalin, tramadol, acetaminophen, and aspirin.

The agents of the invention are used, alone or in combination with one or more other active ingredients, to formulate pharmaceutical compositions of the invention. A pharmaceutical composition of the invention comprises: an effective amount of a pharmaceutical agent in accordance with the invention; and a pharmaceutically acceptable excipient.

A "pharmaceutically acceptable excipient" refers to a substance that is not toxic, biologically intolerable, or otherwise biologically unsuitable for administration to a subject, such as an inert substance, added to a pharmacological composition or otherwise used as a vehicle, carrier, or diluent to facilitate administration of a pharmaceutical agent and that is compatible therewith. Examples of excipients include calcium carbonate, calcium phosphate, various sugars and types of starch, cellulose derivatives, gelatin, vegetable oils and polyethylene glycols.

Delivery forms of the pharmaceutical compositions containing one or more dosage units of the pharmaceutical agents may be prepared using suitable pharmaceutical excipients and compounding techniques now or later known or available to those skilled in the art. The compositions may be administered in the inventive methods by oral, parenteral, rectal, topical, or ocular routes or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the agents may be formulated to yield a dosage of, e.g., from about 0.05 to about 50 mg/kg daily, or from about 0.05 to about 20 mg/kg daily, or from about 0.1 to about 10 mg/kg daily.

Oral tablets may include the active ingredient mixed with pharmaceutically acceptable excipients such as inert diluents, disintegrating agents, binding agents, lubricating agents, sweetening agents, flavoring agents, coloring agents and preservatives agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol or water; preservatives (for example, methyl or propyl p-hydroxybenzoate or sorbic acid); wetting agents such as lecithin; and, if desired, flavoring or coloring agents.

The agents of this invention may also be administered by non-oral routes. For example, the compositions may be formulated for rectal administration as a suppository. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 µg/kg/minute of agent, admixed with a pharmaceutical carrier over a period ranging from several minutes to several days.

For topical administration, the agents may be mixed with a pharmaceutical carrier at a concentration of about 0.1% to about 10% of drug to vehicle. Another mode of administering the agents of the invention may utilize a patch formulation to affect transdermal delivery.

Agents may alternatively be administered in methods of this invention by inhalation, via the nasal or oral routes, e.g., in a spray formulation also containing a suitable carrier.

Exemplary agents useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I).

Scheme A

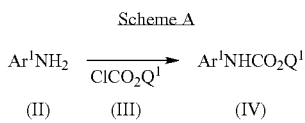

Referring to Scheme A, a compound of formula (IV), in which Ar¹ is as defined in Formula (I), is obtained by reacting a compound for formula (II) with a compound of formula (III), in which Q¹ represents an aryl group. In a preferred embodiment, a compound of formula (II) is reacted with a compound of formula (III), in which Q¹ is substituted or unsubstituted phenyl, in the presence of a base in a solvent at a temperature between 0° C. and 50° C. In a particularly preferred embodiment, a compound of formula (II) is reacted with a compound of formula (III), in which Q¹ is phenyl, in the presence of pyridine in dichloromethane at 0° C. followed by warming to room temperature.

Scheme B

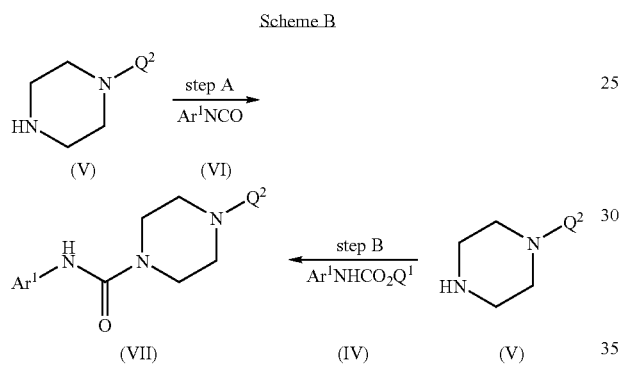

Referring to Scheme B, a compound of formula (VII) is prepared from a compound of formula (V). The variable Q² is either a thiadiazolyl or a nitrogen protecting group. A compound of formula (VII) is obtained by reacting a compound of formula (V) with, a compound of formula (VI). In a preferred embodiment, a compound of formula (V) is reacted with a compound of formula (VI) in a solvent at a temperature between 0° C. and 100° C. In a particularly preferred embodiment, a compound of formula (V) is reacted with a compound of formula (VI) in dichloromethane at room temperature. Alternatively, a compound of formula (VII) is obtained by reacting a compound of formula (V) with a compound of formula (IV). In a preferred embodiment, a compound of formula (V) is reacted with a compound of formula (IV) in a solvent at a temperature between room temperature and 120° C. In a particularly preferred embodiment, a compound of formula (V) is reacted with a compound of formula (IV), in which Ar¹ is phenyl or substituted phenyl, in DMSO in a microwave reactor at 100° C.

Scheme C

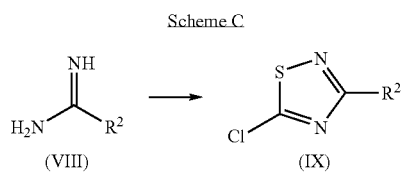

Referring to Scheme C, a compound of formula (IX) is prepared from a compound of formula (VIII). R² is as defined for Formula (I). In a particularly preferred embodiment, a compound of formula (VIII), as a hydrochloride salt, is reacted with perchloro methylmercaptan at 0° C. in the presence of aqueous sodium hydroxide in DCM.

Scheme D

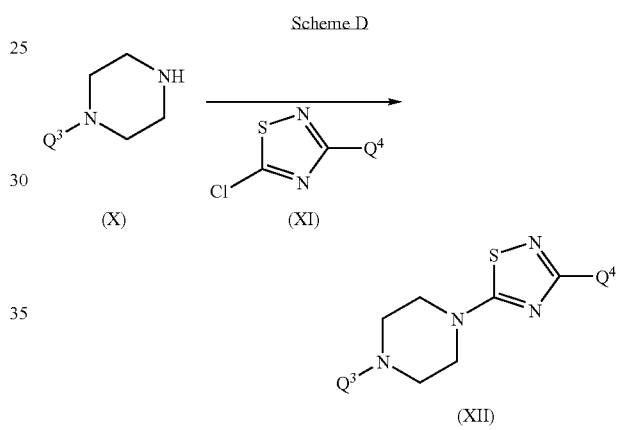

Referring to Scheme D, a compound of formula (XII) is prepared from a compound of formula (X). The variable Q³ represents a nitrogen protecting group, —H, or —CONHAr¹. The variable Q⁴ is either R² or chloro. In a preferred embodiment, a compound of formula (X) is reacted with a compound of formula (XI) in a solvent either in the presence or absence of a base at a temperature between −20° C. and 120° C. In a particularly preferred embodiment, a compound of formula (X) is reacted with a compound of formula (XI) in DCM at a temperature between 0° C. and 25° C.

Scheme E

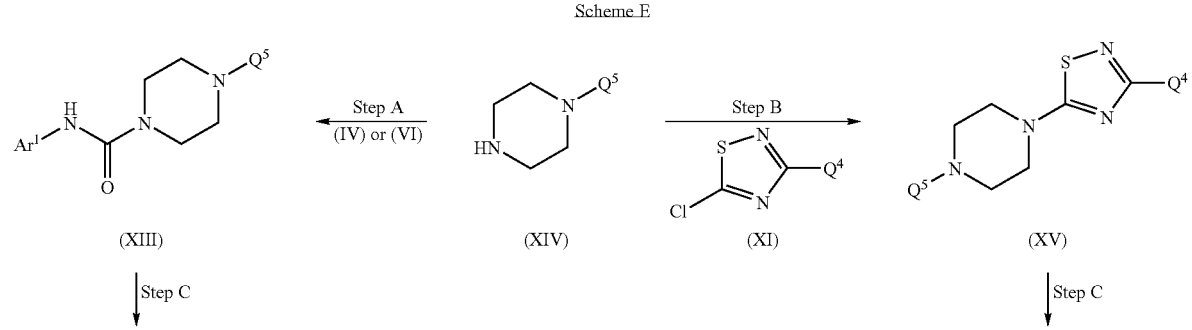

-continued

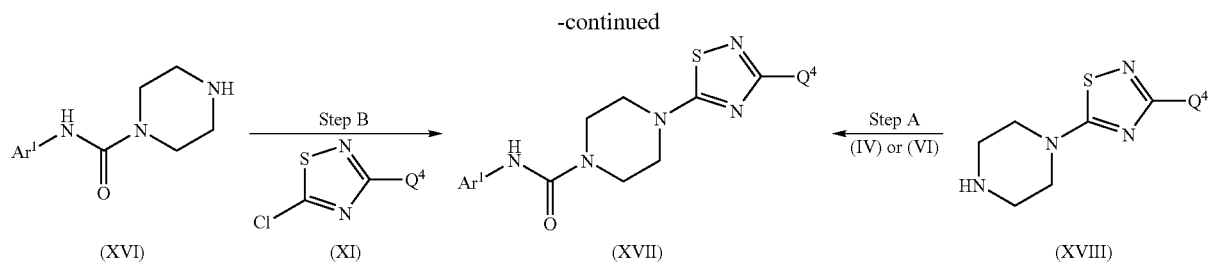

(XVI)　(XI)　(XVII)　(XVIII)

Referring to Scheme E, a compound of formula (XVII) is prepared from a compound of formula (XIV). A nitrogen protecting group $Q^5$ compatible with the transformations in Scheme E is selected. Preferably, $Q^5$ is tert-butyl-carbamoyl. A compound of formula (XIII) is obtained by reacting a compound of formula (XIV) with either a compound of formula (VI) or with a compound of formula (IV) as described in Scheme B. A compound of formula (XVI) is obtained by reacting a compound of formula (XIII) with a reagent capable of removing the protecting group $Q^5$. In a particularly preferred embodiment, a compound of formula (XIII), in which $Q^5$ is tert-butyl-carbamoyl, is reacted with ethereal hydrogen chloride in the presence or absence of methanol at room temperature. A compound of formula (XVII) is obtained by reacting a compound of formula (XVI) with a compound of formula (XI) in analogy with Scheme D. A compound of formula (XV) is obtained by reacting a compound of formula (XIV) with a compound of formula (XI) in analogy with Scheme D. A compound of formula (XVIII) is obtained by reacting a compound of formula (XV) under deprotection conditions as shown in Step C of Scheme E. A compound of formula (XVII) is obtained by reacting a compound of formula (XVIII) with either a compound of formula (VI) or with a compound of formula (IV) as described in Scheme B.

Scheme F

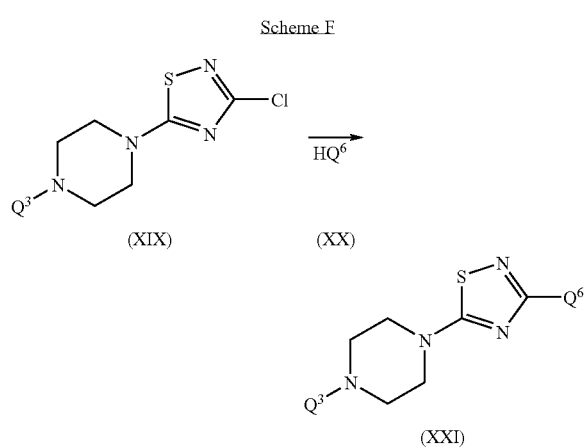

(XIX)　(XX)

(XXI)

Referring to Scheme F, a compound of formula (XXI) is prepared from a compound of formula (XIX). The variable $Q^6$ may be $R^3$ or $R^4$ as defined in Formula (I). In a preferred embodiment, a compound of formula (XIX) is reacted with a compound of formula (XX), in a solvent or neat, in the presence or absence of a base at a temperature between $-20°$ C. and $120°$ C. In a particularly preferred embodiment, a compound of formula (XIX) is reacted with a compound of formula (XX) neat at $120°$ C. in a microwave reactor.

Scheme G (XIX)　(XXII)

(XXIII)

Referring to Scheme G, a compound of formula (XXIII) is prepared from a compound of formula (XIX). In a preferred embodiment, a compound of formula (XIX) is reacted with a compound of formula (XXII), a base, and a catalyst in a solvent at a temperature between $0°$ C. and $150°$ C. In a particularly preferred embodiment, a compound of formula (XIX) is reacted with a compound of formula (XXII) in the presence of dichlorobis(triphenylphosphine)palladium, aqueous sodium carbonate and tetra-n-butylammonium bromide in a mixture of toluene and ethanol at $120°$ C. in a microwave reactor.

The following specific examples are provided to further illustrate the invention and various preferred embodiments.

EXAMPLES

Chemistry:

In obtaining the characterization data described in the examples below, the following analytical protocols were followed as indicated.

NMR spectra were obtained on Brucker model DRX spectrometers. The format of the $^1$H NMR data below is: chemical shift in ppm downfield of the tetramethylsilane reference (multiplicity, coupling constant J in Hz, integration). Silica gel was used for all preparative chromatography unless otherwise noted. Where solutions were "concentrated", they were concentrated using a rotary evaporator under reduced pressure.

Intermediates 1-17 describe the synthesis of intermediate compounds used to prepare certain compounds of the invention.

Intermediate 1

4-Phenylcarbamoyl-piperazine-1-carboxylic acid tert-butyl ester

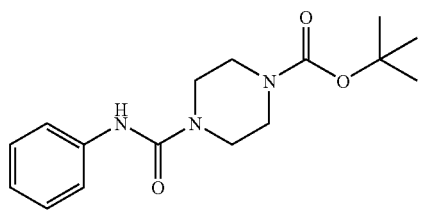

A 0° C. solution of piperazine-1-carboxylic acid tert-butyl ester (114 g) in DCM (500 mL) was treated with phenyl isocyanate (65 mL). After 1 hour (h), the mixture was allowed to warm to room temperature (rt). After 15 h, the resulting mixture was filtered and the solid was washed with DCM (2×100 mL), giving the title compound as a white amorphous solid (95 g).

Intermediate 2

Piperazine-1-carboxylic acid phenylamide

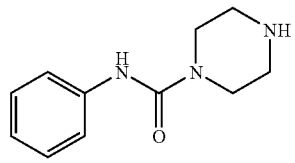

A solution of Intermediate 1 (50 g) in MeOH (1 L) was treated with HCl (2.0 M in Et$_2$O, 164 mL). After 48 h, the resulting suspension was diluted with Et$_2$O (1 L) and filtered. The solid was washed with Et$_2$O (3×100 mL) and dried in vacuo, giving a white powder (32 g). This powder was partitioned between DCM (400 mL) and 10% aq. KOH (400 mL). The aqueous phase was extracted with DCM (2×400 mL). The organic phases were combined, dried (MgSO$_4$), and concentrated, giving the title compound as a white amorphous solid (26 g).

Intermediate 3

Pyridin-4-yl-carbamic acid phenyl ester

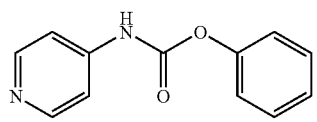

To a suspension of 4-aminopyridine (0.941 g) in THF (10 mL) was added dropwise phenyl chloroformate (2×0.25 mL) at 0° C. The mixture was allowed to warm to rt overnight. The mixture was diluted with EtOAc (30 mL) and washed with saturated (satd.) aq. NaHCO$_3$. The organic layer was dried (MgSO$_4$) and concentrated. Chromatography of the residue (0-5% 2 M NH$_3$ in MeOH-DCM) gave a the title compound as a white solid (0.74 g).

Intermediates 4-7 were prepared in analogy to Intermediate 3, using the appropriate amine in place of 4-aminopyridine.

Intermediate 4

Pyridin-3-yl-carbamic acid phenyl ester

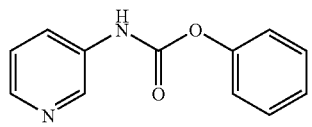

The title compound was prepared from 3-aminopyridine.

Intermediate 5

Pyridin-2-yl-carbamic acid phenyl ester

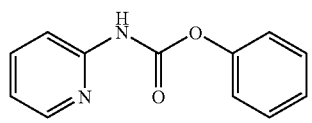

The title compound was prepared from 2-aminopyridine.

Intermediate 6

Pyrimidin-2-yl-carbamic acid phenyl ester

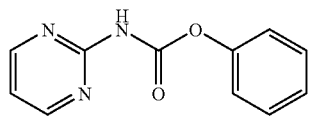

The title compound was prepared from 2-aminopyrimidine.

Intermediate 7

Thiazol-2-yl-carbamic acid phenyl ester

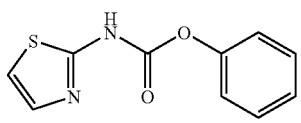

The title compound was prepared from 2-aminothiazole.

Intermediate 8

1-(5-Phenyl-[1,2,4]thiadiazol-3-yl)-piperazine

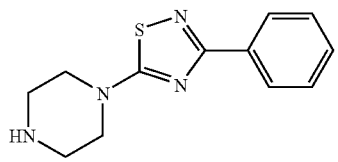

To a mixture of benzamidine hydrochloride (470 mg) in DCM (5 mL) was added perchloromethyl mercaptan (558 mg) at rt. The reaction mixture was cooled to 0° C. and treated with 6 N NaOH (3 mL). After 30 min, the organic layer was washed with water (10 mL), cooled in a water bath, treated with piperazine (775 mg), and stirred overnight. The reaction mixture was filtered to remove insoluble material. The filtrate was washed with water (10 mL), brine (10 mL), filtered, dried (MgSO$_4$), and concentrated. Chromatography of the residue (0-7% 2 M NH$_3$ in MeOH-DCM) gave the title compound as a white solid (360 mg).

Intermediates 9-11 were prepared in analogy with Intermediate 8 using the specified amidine hydrochloride and piperazine. Products were either isolated by chromatography (2 M NH$_3$ in MeOH-DCM) or used directly without purification.

Intermediate 9

1-[3-(4-Chloro-phenyl)-[1,2,4]thiadiazol-5-yl]-piperazine

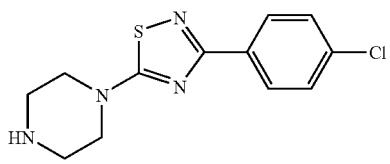

The title compound was prepared from 4-chlorobenzamidine hydrochloride.

Intermediate 10

1-(3-p-Tolyl-[1,2,4]thiadiazol-5-yl)-piperazine

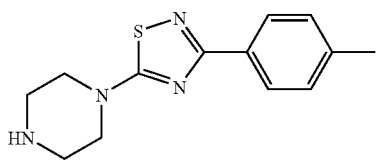

The title compound was prepared from 4-methylbenzamidine hydrochloride.

Intermediate 11

1-[3-(4-Methoxy-phenyl)-[1,2,4]thiadiazol-5-yl]-piperazine

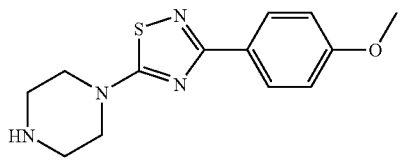

The title compound was prepared from 4-methoxybenzamidine hydrochloride.

Intermediate 12

4-(3-Chloro-[1,2,4]thiadiazol-5-yl)-piperazine-1-carboxylic acid phenylamide

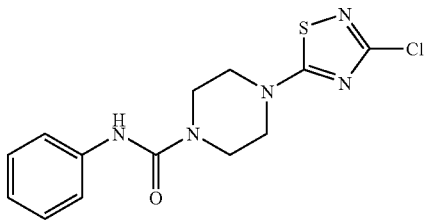

To a water bath-cooled solution of 3,5-dichloro-1,2,4-thiadiazole (1.6 g) in DCM (5 mL) was added dropwise a solution of Intermediate 2 (2.4 g) in DCM (8 mL), followed by DIPEA (1.9 mL). The resulting suspension was stirred overnight and filtered. The filtrate was diluted with DCM (50 mL), washed with water (10 mL), dried (MgSO$_4$), and concentrated. Chromatography of the residue (50% EtOAc-hexanes) gave the title compound as a white solid (2.3 g).

Intermediate 13

5-Chloro-3-(4-fluoro-phenyl)-[1,2,4]thiadiazole

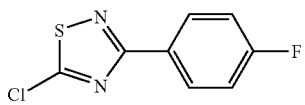

To a suspension of 4-fluorobenzamidine hydrochloride (0.385 g) in DCM (5 mL) was added perchloromethyl mercaptan (0.219 mL). The resulting mixture was cooled to 0° C., treated with 6 N NaOH (2 mL) and stirred for 30 min. The resulting mixture was diluted with water (10 mL) and extracted with DCM (20 mL). The organic layer was dried (MgSO$_4$) and concentrated. Chromatography of the residue (0-20% EtOAc-hexanes) gave the title compound as a yellow-orange solid (0.43 g).

Intermediate 14

1-(3-Piperidin-1-yl-[1,2,4]thiadiazol-5-yl)-piperazine

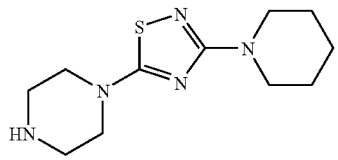

A mixture of Intermediate 12 (0.162 g) and piperidine (0.247 mL) was heated in a microwave reactor at 120° C. for 20 min. The resulting mixture was concentrated. Chromatography of the residue (0-5% 2 M $NH_3$ in MeOH-DCM) gave the title compound as a colorless oil (0.130 g).

Intermediates 15-17 were prepared in analogy with Intermediate 14 using the specified amine and the product of Intermediate 12.

Intermediate 15

1-[3-(4-Methyl-piperidin-1-yl)-[1,2,4]thiadiazol-5-yl]-piperazine

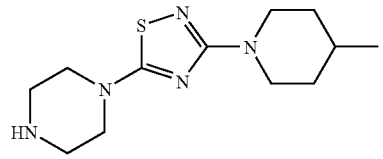

The title compound was prepared from 4-methylpiperidine.

Intermediate 16

1-[3-(4-Methyl-piperazin-1-yl)-[1,2,4]thiadiazol-5-yl]-piperidine

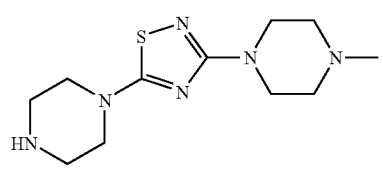

The title compound was prepared from N-methylpiperazine.

Intermediate 17

1-(3-Pyrrolidin-1-yl-[1,2,4]thiadiazol-5-yl)-piperazine

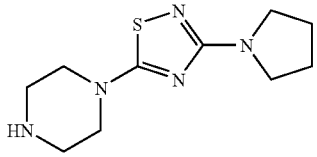

The title compound was prepared from pyrrolidine.

Example 1

4-(3-Phenyl-[1,2,4]thiadiazol-5-yl)-piperazine-1-carboxylic acid phenylamide (CAS No. 681136-29-8)

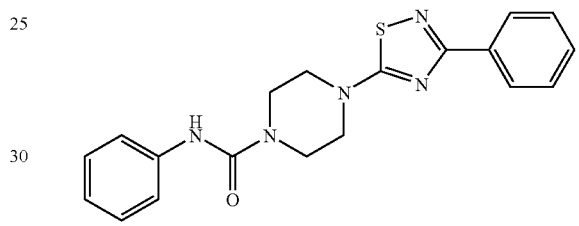

A solution of Intermediate 8 (246 mg) in DCM (3 mL) was treated with phenyl isocyanate (0.13 mL). After 16 h, the resulting suspension was filtered, and the solid was washed with DCM (1×1 mL), giving the title compound as a white solid. $^1$H NMR (400 MHz, $CDCl_3$): 8.21-8.17 (m, 2H), 7.46-7.21 (m, 7H), 7.11-7.06 (m, 1H), 6.59 (br s, 1H), 3.66 (s, 8H).

Example 1 was alternatively prepared from Intermediate 12 and phenylboronic acid under Suzuki coupling conditions as outlined in Scheme G.

Examples 2-30 were prepared in analogy with Example 1 using the specified N-arylpiperazines and isocyanates, with purification by filtration or chromatography.

Example 2

4-(3-Phenyl-[1,2,4]thiadiazol-5-yl)-piperazine-1-carboxylic acid (2-chloro-phenyl)-amide

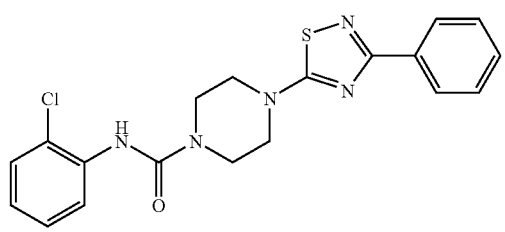

The title compound was prepared from Intermediate 8 and 2-chlorophenyl isocyanate. $^1$H NMR (400 MHz, $CDCl_3$): 8.21-8.16 (m, 3H), 7.45-7.43 (m, 3H), 7.38-7.35 (m, 1H), 7.30-7.28 (m, 1H), 7.04-6.98 (m, 2H), 3.76 (s, 8H).

Example 3

4-(3-Phenyl-[1,2,4]thiadiazol-5-yl)-piperazine-1-carboxylic acid (3-fluoro-phenyl)-amide

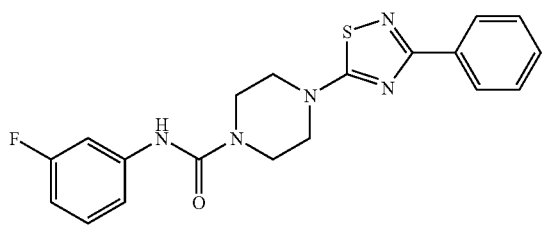

The title compound was prepared from Intermediate 8 and 3-fluorophenyl isocyanate. $^1$H NMR (400 MHz, CDCl$_3$): 8.21-8.17 (m, 2H), 7.45-7.42 (m, 3H), 7.33-7.22 (m, 2H), 7.04-7.01 (m, 1H), 6.80-6.75 (m, 1H), 6.47 (s, 1H), 3.71 (s, 8H).

Example 4

4-(3-Phenyl-[1,2,4]thiadiazol-5-yl)-piperazine-1-carboxylic acid (4-fluoro-phenyl)-amide

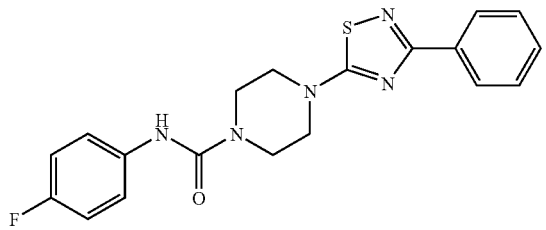

The title compound was prepared from Intermediate 8 and 4-fluorophenyl isocyanate. $^1$H NMR (400 MHz, CDCl$_3$): 8.21-8.17 (m, 2H), 7.45-7.43 (m, 3H), 7.33-7.29 (m, 2H), 7.05-7.00 (m, 2H), 6.37 (s, 1H), 3.71 (s, 8H).

Example 5

4-(3-Phenyl-[1,2,4]thiadiazol-5-yl)-piperazine-1-carboxylic acid (4-methoxy-phenyl)-amide

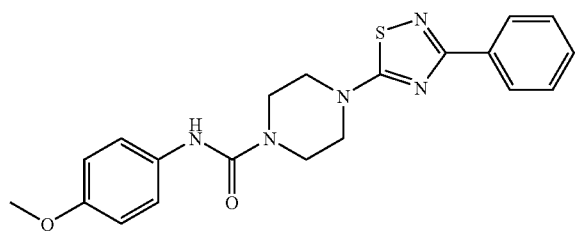

The title compound was prepared from Intermediate 8 and 4-methoxyphenyl isocyanate. $^1$H NMR (400 MHz, CDCl$_3$): 8.21-8.18 (m, 2H), 7.45-7.42 (m, 3H), 7.27-7.23 (m, 2H), 6.88-6.85 (m, 2H), 6.28 (s, 1H), 3.79 (s, 3H), 3.69 (s, 8H).

Example 6

4-(3-Phenyl-[1,2,4]thiadiazol-5-yl)-piperazine-1-carboxylic acid (4-benzyloxy-phenyl)-amide

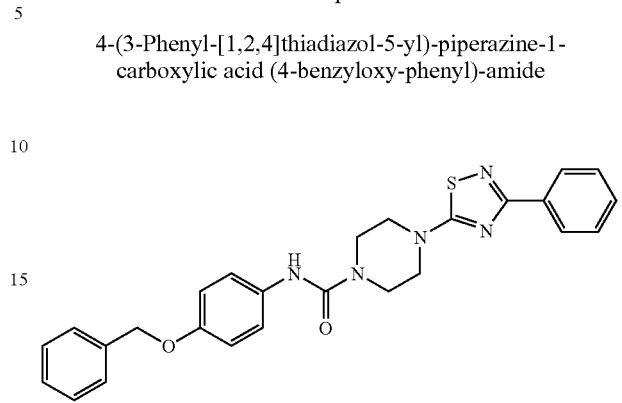

The title compound was prepared from Intermediate 8 and 4-benzyloxyphenyl isocyanate. $^1$H NMR (400 MHz, CDCl$_3$): 8.21-8.18 (m, 2H), 7.45-7.23 (m, 10H), 6.96-6.93 (m, 2H), 6.26 (s, 1H), 5.05 (s, 2H), 3.70 (s, 8H).

Example 7

4-(3-Phenyl-[1,2,4]thiadiazol-5-yl)-piperazine-1-carboxylic acid m-tolylamide

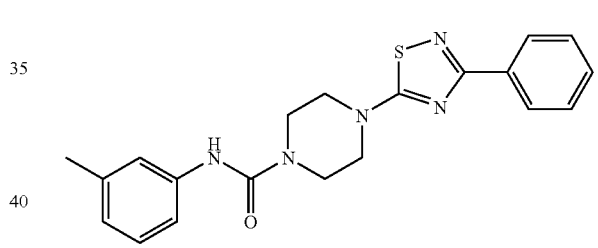

The title compound was prepared from Intermediate 8 and 3-methylphenyl isocyanate. $^1$H NMR (400 MHz, CDCl$_3$): 8.21-8.18 (m, 2H), 7.45-7.23 (m, 10H), 6.96-6.93 (m, 2H), 6.26 (s, 1H), 5.05 (s, 2H), 3.70 (s, 8H).

Example 8

4-(3-Phenyl-[1,2,4]thiadiazol-5-yl)-piperazine-1-carboxylic acid (2-nitro-phenyl)-amide

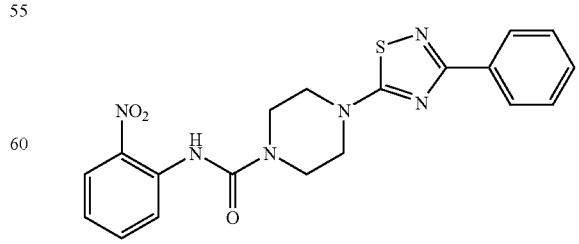

The title compound was prepared from Intermediate 8 and 2-nitrophenyl isocyanate. $^1$H NMR (400 MHz, CDCl$_3$):

10.35 (s, 1H), 8.65-8.62 (m, 1H), 8.25-8.19 (m, 3H), 7.67-7.62 (m, 1H), 7.46-7.42 (m, 3H), 7.14-7.10 (m, 1H), 3.83-3.75 (m, 8H).

Example 9

4-(3-Phenyl-[1,2,4]thiadiazol-5-yl)-piperazine-1-carboxylic acid (2-methoxy-phenyl)-amide

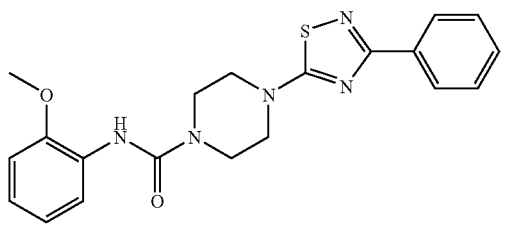

The title compound was prepared from Intermediate 8 and 2-methoxyphenyl isocyanate. $^1$H NMR (400 MHz, CDCl$_3$): 8.21-8.18 (m, 2H), 8.14-8.11 (m, 1H), 7.45-7.42 (m, 3H), 7.15 (s, 1H), 7.02-6.95 (m, 2H), 6.89-6.87 (m, 1H), 3.90 (s, 3H), 3.72 (s, 8H).

Example 10

4-(3-Phenyl-[1,2,4]thiadiazol-5-yl)-piperazine-1-carboxylic acid (3-chloro-phenyl)-amide

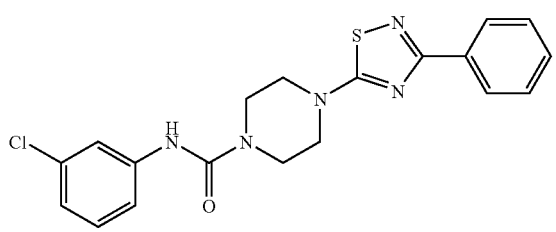

The title compound was prepared from Intermediate 8 and 3-chlorophenyl isocyanate. $^1$H NMR (400 MHz, CDCl$_3$): 8.21-8.18 (m, 2H), 7.48-7.42 (m, 4H), 7.21-7.24 (m, 2H), 7.07-7.05 (m, 1H), 6.45 (s, 1H), 3.71 (s, 8H).

Example 11

4-(3-Phenyl-[1,2,4]thiadiazol-5-yl)-piperazine-1-carboxylic acid p-tolylamide

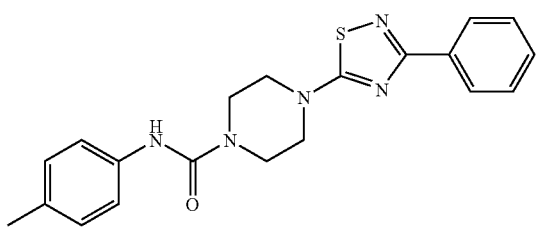

The title compound was prepared from Intermediate 8 and 4-methylphenyl isocyanate. $^1$H NMR (400 MHz, CDCl$_3$): 8.21-8.18 (m, 2H), 7.45-7.42 (m, 3H), 7.25-7.22 (m, 2H), 7.13-7.11 (m, 2H), 6.37 (s, 1H), 3.69 (s, 1H), 2.31 (s, 1H).

Example 12

4-(3-Phenyl-[1,2,4]thiadiazol-5-yl)-piperazine-1-carboxylic acid o-tolylamide

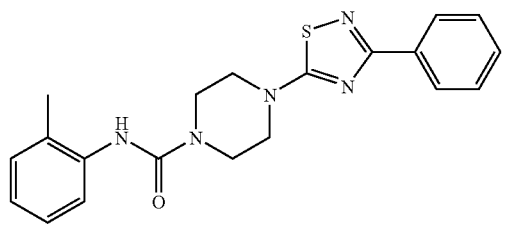

The title compound was prepared from Intermediate 8 and 2-methylphenyl isocyanate. $^1$H NMR (400 MHz, CDCl$_3$): 8.21-8.17 (m, 2H), 7.58-7.52 (m, 1H), 7.47-7.41 (m, 3H), 7.23-7.19 (m, 2H), 7.09-7.05 (m, 1H), 6.16 (s, 1H), 3.71 (s, 8H), 2.28 (s, 3H).

Example 13

4-(3-Phenyl-[1,2,4]thiadiazol-5-yl)-piperazine-1-carboxylic acid (2-methylsulfanyl-phenyl)-amide

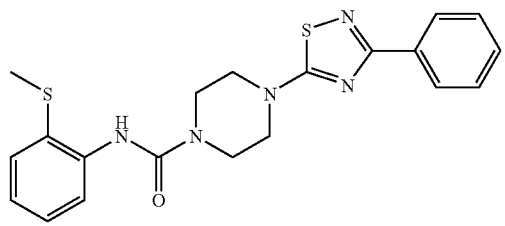

The title compound prepared from Intermediate 8 and 1-isocyanato-2-methylsulfanyl-benzene. $^1$H NMR (400 MHz, CDCl$_3$): 8.21-8.14 (m, 3H), 7.50-7.42 (m, 1H), 7.33-7.28 (m, 2H), 7.05-7.00 (m, 1H), 3.79-3.74 (m, 8H), 2.39 (s, 3H).

Example 14

4-(3-Phenyl-[1,2,4]thiadiazol-5-yl)-piperazine-1-carboxylic acid (3-methoxy-phenyl)-amide

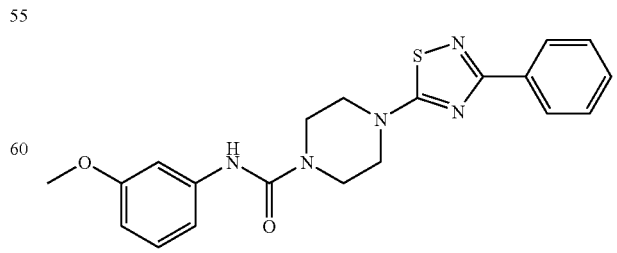

The title compound was prepared from Intermediate 8 and 4-methoxyphenyl isocyanate. $^1$H NMR (400 MHz, CDCl$_3$):

8.19-8.15 (m, 2H), 7.46-7.40 (m, 4H), 7.27-7.23 (m, 1H), 7.31-6.70 (m, 3H), 4.00-3.97 (m, 4H), 3.80 (s, 3H), 3.79-3.69 (m, 4H).

Example 15

4-(3-Phenyl-[1,2,4]thiadiazol-5-yl)-piperazine-1-carboxylic acid biphenyl-4-ylamide

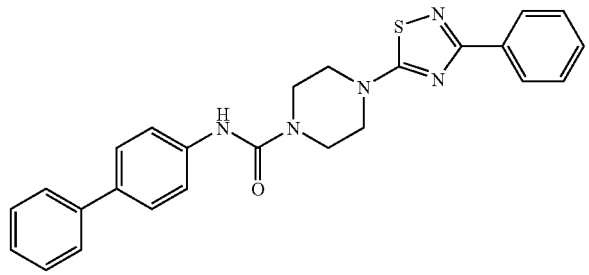

The title compound was prepared from Intermediate 8 and 4-isocyanato-biphenyl. $^1$H NMR (400 MHz, CDCl$_3$): 8.21-8.19 (m, 2H), 7.59-7.54 (m, 4H), 7.45-7.30 (m, 8H), 6.51 (s, 1H), 3.72 (s, 8H).

Example 16

4-(3-Phenyl-[1,2,4]thiadiazol-5-yl)-piperazine-1-carboxylic acid naphthalen-2-ylamide

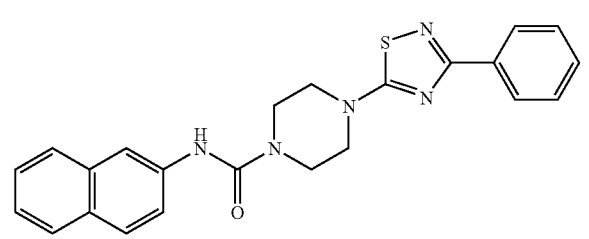

The title compound was prepared from Intermediate 8 and 2-naphthyl isocyanate. $^1$H NMR (400 MHz, CDCl$_3$): 8.21-8.19 (m, 2H), 7.57 (d, J=2.0 Hz, 1H), 7.80-7.75 (m, 3H), 7.47-7.37 (m, 6H), 6.63 (s, 1H), 3.74-3.68 (m, 8H).

Example 17

4-(3-Phenyl-[1,2,4]thiadiazol-5-yl)-piperazine-1-carboxylic acid (4-ethoxy-phenyl)-amide

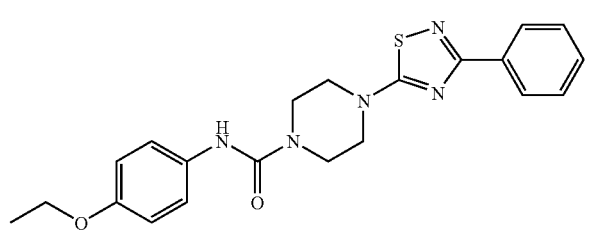

The title compound was prepared from Intermediate 8 and 4-ethoxyphenyl isocyanate. $^1$H NMR (400 MHz, CDCl$_3$): 8.21-8.18 (m, 2H), 7.45-7.42 (m, 3H), 7.25-7.22 (m, 2H), 6.87-6.84 (m, 2H), 6.31 (s, 1H), 4.00 (m, 2H), 3.68 (s, 8H), 1.40 (t, J=7.0 Hz, 3H).

Example 18

4-(3-p-Tolyl-[1,2,4]thiadiazol-5-yl)-piperazine-1-carboxylic acid phenylamide

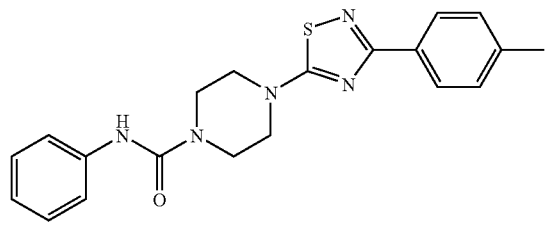

The title compound was prepared from Intermediate 10 and phenyl isocyanate. $^1$H NMR (400 MHz, CDCl$_3$): 8.08 (d, J=8.1 Hz, 2H), 7.38-7.30 (m, 6H), 7.11-7.06 (m, 1H), 6.39 (s, 1H), 3.71 (s, 8H), 2.40 (s, 3H).

Example 19

4-[3-(4-Methoxy-phenyl)-[1,2,4]thiadiazol-5-yl]-piperazine-1-carboxylic acid phenylamide

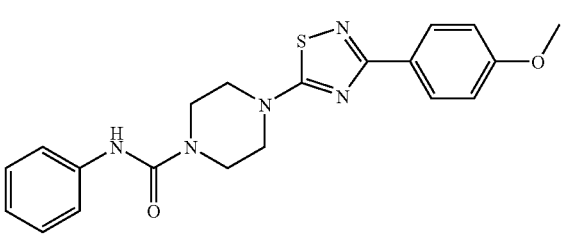

The title compound was prepared from Intermediate 11 and phenyl isocyanate. $^1$H NMR (400 MHz, CDCl$_3$): 8.16-8.12 (m, 2H), 7.37-7.30 (m, 4H), 7.10-7.06 (m, 1H), 6.96-6.93 (m, 2H), 6.42 (s, 1H), 3.86 (s, 3H), 3.69 (s, 8H).

Example 20

4-[3-(4-Chloro-phenyl)-[1,2,4]thiadiazol-5-yl]-piperazine-1-carboxylic acid phenylamide

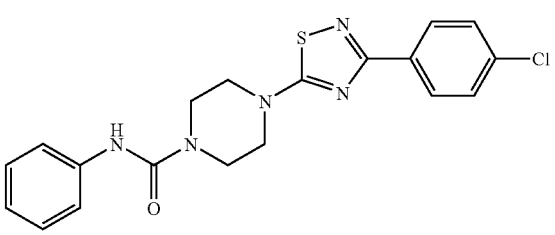

The title compound was prepared from Intermediate 9 and phenyl isocyanate. ¹H NMR (400 MHz, CDCl₃): 8.15-8.12 (m, 2H), 7.42-7.26 (m, 6H), 7.11-7.07 (m, 1H), 6.39 (s, 1H), 5.30 (s, 8H).

Example 21

4-(3-Phenyl-[1,2,4]thiadiazol-5-yl)-piperazine-1-carboxylic acid (2-fluoro-phenyl)-amide

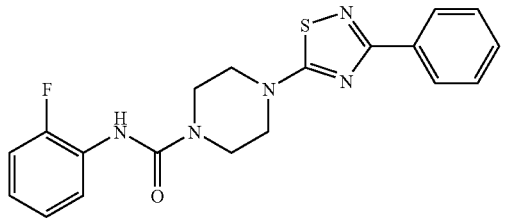

The title compound was prepared from Intermediate 8 and 2-fluorophenyl isocyanate. ¹H NMR (400 MHz, CDCl₃): 8.21-8.18 (m, 2H), 8.09-8.04 (m, 1H), 7.45-7.42 (m, 3H), 7.15-6.98 (m, 3H), 6.64-6.63 (m, 1H), 2.74 (s, 8H).

Example 22

4-(3-Phenyl-[1,2,4]thiadiazol-5-yl)-piperazine-1-carboxylic acid (4-chloro-phenyl)-amide

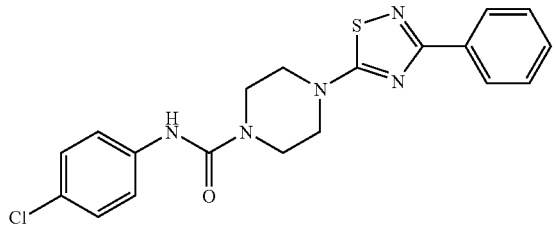

The title compound was prepared from Intermediate 8 and 4-chlorophenyl isocyanate. ¹H NMR (400 MHz, CDCl₃): 8.20-8.17 (m, 2H), 7.45-7.42 (m, 3H), 7.33-7.25 (m, 4H), 6.49 (s, 1H), 3.69 (s, 8H).

Example 23

4-(3-Phenyl-[1,2,4]thiadiazol-5-yl)-piperazine-1-carboxylic acid (2-isopropyl-phenyl)-amide

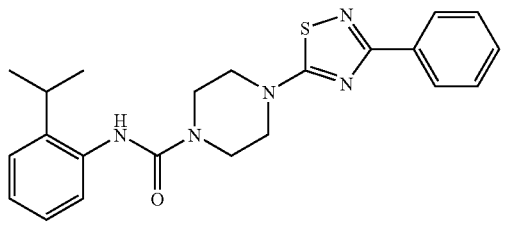

The title compound was prepared from Intermediate 8 and 2-isopropylphenyl isocyanate. ¹H NMR (400 MHz, CDCl₃): 8.21-8.18 (m, 2H), 7.50-7.42 (m, 4H), 7.31-7.15 (m, 3H), 6.20 (s, 1H), 3.73-3.68 (m, 8H), 3.08-3.01 (m, 1H), 1.27 (d, J=6.8 Hz, 6H).

Example 24

4-(3-Phenyl-[1,2,4]thiadiazol-5-yl)-piperazine-1-carboxylic acid (2-trifluoromethyl-phenyl)-amide

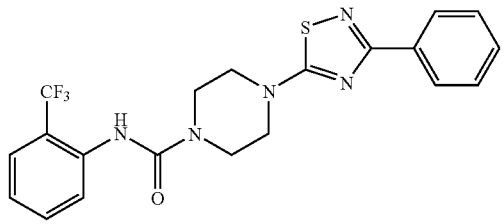

The title compound was prepared from Intermediate 8 and 2-trifluoromethylphenyl isocyanate. ¹H NMR (400 MHz, CDCl₃): 8.21-8.18 (m, 2H), 8.07 (d, J=8.1 Hz, 1H), 7.61-7.52 (m, 2H), 7.45-7.42 (m, 3H), 7.21-7.17 (m, 1H), 6.81 (s, 1H), 3.75-3.70 (m, 8H).

Example 25

4-(3-Phenyl-[1,2,4]thiadiazol-5-yl)-piperazine-1-carboxylic acid (4-nitro-phenyl)-amide

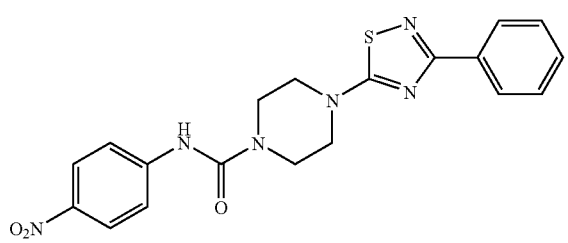

The title compound was prepared from Intermediate 8 and 4-nitrophenyl isocyanate. ¹H NMR (400 MHz, CDCl₃): 8.25-8.07 (m, 4H), 7.58-7.54 (m, 2H), 7.46-7.42 (m, 3H), 6.72 (s, 1H), 3.75 (s, 8H).

Example 26

4-(3-Phenyl-[1,2,4]thiadiazol-5-yl)-piperazine-1-carboxylic acid (4-dimethylamino-phenyl)-amide

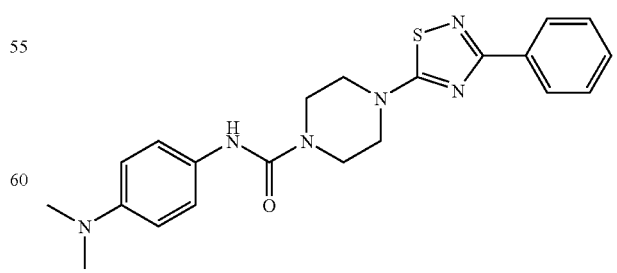

The title compound was prepared from Intermediate 8 and 4-N,N-dimethylaminophenyl isocyanate. ¹H NMR (400

MHz, CDCl₃): 8.21-8.18 (m, 2H), 7.45-7.41 (m, 3H), 7.19 (d, J=8.3 Hz, 2H), 6.71 (br s, 2H), 6.20 (br s, 1H), 3.68 (br s, 8H), 2.91 (s, 6H).

Example 27

4-(3-Piperidin-1-yl-[1,2,4]thiadiazol-5-yl)-piperazine-1-carboxylic acid phenylamide

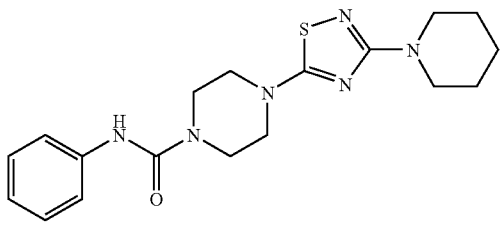

The title compound was prepared from Intermediate 14 and phenyl isocyanate. ¹H NMR (400 MHz, CDCl₃): 7.36-7.29 (m, 4H), 7.10-7.05 (m, 1H), 6.34 (s, 1H), 3.69-3.53 (m, 16H), 1.63-1.58 (m, 2H).

Example 28

4-(3-Pyrrolidin-1-yl-[1,2,4]thiadiazol-5-yl)-piperazine-1-carboxylic acid phenylamide

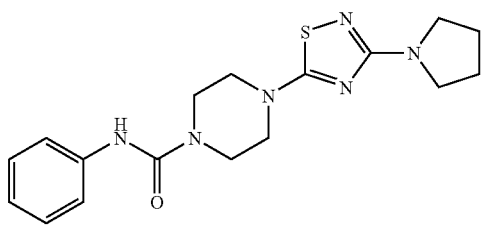

The title compound was prepared from Intermediate 17 and phenyl isocyanate. ¹H NMR (400 MHz, CDCl₃): 7.36-7.29 (m, 4H), 7.10-7.05 (m, 1H), 6.37 (s, 1H), 3.65-3.62 (m, 4H), 3.58-3.52 (m, 8H), 1.95-1.91 (m, 4H).

Example 29

4-[3-(4-Methyl-piperidin-1-yl)-[1,2,4]thiadiazol-5-yl]-piperazine-1-carboxylic acid phenylamide

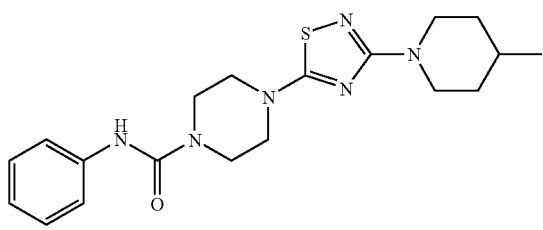

The title compound was prepared from Intermediate 16 and phenyl isocyanate. ¹H NMR (400 MHz, CDCl₃): 7.36-7.29 (m, 4H), 7.10-7.05 (m, 1H), 6.37 (s, 1H), 4.31-4.28 (m, 2H), 3.64-3.60 (m, 4H), 3.57-3.52 (m, 4H), 2.91-2.83 (m, 2H), 1.67-1.64 (m, 2H), 1.57-1.50 (m, 1H), 1.26-1.16 (m, 2H), 0.96 (d, J=8.1 Hz, 3H).

Example 30

4-{[4-(3-Phenyl-[1,2,4]thiadiazol-5-yl)-piperazine-1-carbonyl]-amino}-benzoic acid methyl ester The title compound was prepared from Intermediate 8 and 4-isocyanato-benzoic acid methyl ester. ¹H NMR (400 MHz, CDCl₃): 10.9 (s, 1H), 8.56-8.54 (m, 1H), 8.22-8.19 (m, 2H), 8.04-8.01 (m, 1H), 7.56-7.52 (m, 1H), 7.45-7.42 (m, 3H), 7.03-7.00 (m, 1H), 3.93 (s, 3H), 3.83-3.72 (m, 8H).

Example 31

4-(3-Phenyl-[1,2,4]thiadiazol-5-yl)-piperazine-1-carboxylic acid pyrimidin-2-ylamide A solution of Intermediate 6 (0.1 g) and Intermediate 8 (0.12 g) in DMSO (0.5 mL) was heated in a microwave reactor at 100° C for 30 min. The reaction mixture was partitioned between DCM and water. The organic layer was washed with brine (3×), dried (Na₂SO₄), and concentrated. Chromatography of the residue (5% 2 M NH₃ in MeOH-DCM) gave the title compound (0.12 g). ¹H NMR (400 MHz, CDCl₃): 8.57 (d, J=5.0 Hz, 2H), 8.17 (m, 2H), 7.41 (m, 3H), 6.97 (t, J=5.0 Hz, 1H), 3.77 (m, 4H), 3.71 (m, 4H).

Example 32

4-(3-Phenyl-[1,2,4]thiadiazol-5-yl)-piperazine-1-carboxylic acid thiazol-2-ylamide

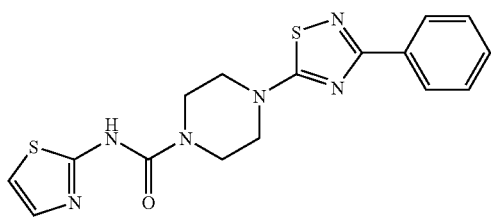

The title compound was prepared in analogy with Example 31 from Intermediate 8 and Intermediate 7. $^1$H NMR (400 MHz, CDCl$_3$): 8.24-8.20 (m, 2H), 7.55-7.45 (m, 4H), 7.00 (d, J=3.7 Hz, 1H), 3.94-3.83 (m, 4H), 3.80-3.72 (m, 4H).

Example 33

4-(3-Phenyl-[1,2,4]thiadiazol-5-yl)-piperazine-1-carboxylic acid pyridin-4-ylamide

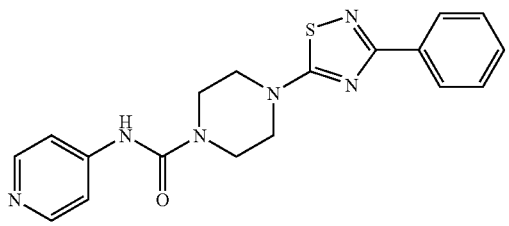

A mixture of Intermediate 3 (0.107 g) and Intermediate 8 (0.123 g) in DMSO (2 mL) was stirred at rt overnight. The resulting mixture was diluted with EtOAc (30 mL) and washed with satd. aq. NaHCO$_3$ (10 mL). The organic layer was dried (MgSO$_4$) and concentrated. Chromatography of the residue (0-5% 2 M NH$_3$ in MeOH-DCM) gave the title compound as a white solid (0.16 g). $^1$H NMR (400 MHz, CDCl$_3$): 8.46-8.45 (m, 2H), 8.20-8.17 (m, 2H), 7.44-7.42 (m, 3H), 7.38-7.35 (m, 2H), 6.94 (s, 1H), 3.75-3.69 (m, 8H).

Example 34

4-(3-Phenyl-[1,2,4]thiadiazol-5-yl)-piperazine-1-carboxylic acid pyridin-2-ylamide

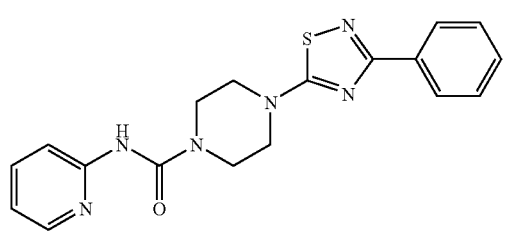

The title compound was prepared in analogy with Example 33 from Intermediate 5 and Intermediate 8. $^1$H NMR (400 MHz, CDCl$_3$): 8.22-8.17 (m, 3H), 8.02 (d, J=8.6 Hz, 1H), 7.71-7.66 (m, 1H), 7.45-7.42 (m, 3H), 7.31 (s, 1H), 7.00-6.97 (m, 1H), 3.76-3.70 (m, 8H).

Example 35

4-(3-Phenyl-[1,2,4]thiadiazol-5-yl)-piperazine-1-carboxylic acid pyridin-3-ylamide

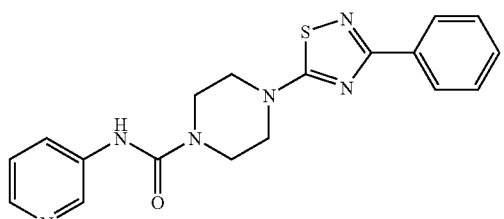

The title compound was prepared in analogy with Example 33 from Intermediate 4 and Intermediate 8. $^1$H NMR (400 MHz, CDCl$_3$): 8.48 (d, J=3.0 Hz, 1H), 8.34-8.32 (m, 1H), 8.21-8.18 (m, 2H), 8.00-7.97 (m, 1H), 7.46-7.42 (m, 3H), 7.30-7.27 (m, 1H), 6.44 (s, 1H), 3.75 (s, 8H).

Example 36

4-[3-(4-Fluoro-phenyl)-[1,2,4]thiadiazol-5-yl]-piperazine-1-carboxylic acid phenylamide

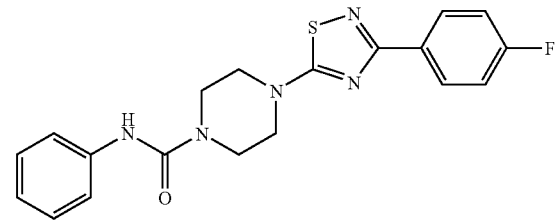

A mixture of Intermediate 13 (0.42 g), Intermediate 2 (0.41 g), and DIEA (0.79 mL) in acetonitrile (5 mL) was heated at reflux for 24 h. The mixture was cooled to rt and concentrated. Chromatography of the residue (0-50% EtOAc-hexanes) gave the title compound as a light brown solid (0.31 g). $^1$H NMR (400 MHz, CDCl$_3$): 8.20-8.16 (m, 2H), 7.38-7.30 (m, 4H), 7.13-7.07 (m, 3H), 6.37 (s, 1H), 3.71 (s, 8H).

Example 37

4-[3-(3-Nitro-phenyl)-[1,2,4]thiadiazol-5-yl]-piperazine-1-carboxylic acid phenylamide

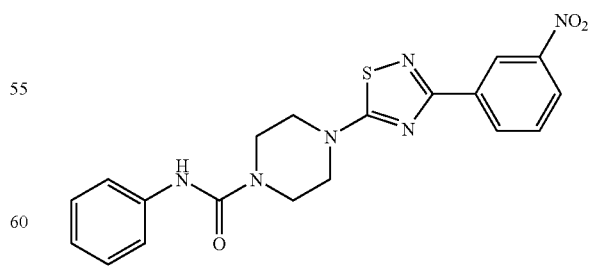

To a suspension of 3-nitrobenzamidine hydrochloride (0.403 g) in DCM (5 mL) was added perchloromethyl mercaptan (0.219 mL). The resulting mixture was cooled to 0° C. and treated with 6 N NaOH (2 mL). After 30 min, the mixture was warmed to rt, treated with water (5 mL), and extracted with DCM (5 mL). The combined organic extracts were washed with water (5 mL). The solution was cooled in a water bath and treated with Intermediate 2 (410 mg) and DIEA (0.348 mL). The mixture was stirred overnight. The resulting suspension was filtered, and the filtrate was treated with water (10 mL) and extracted with DCM (20 mL). The organic layer was dried (MgSO$_4$) and concentrated. Chromatography of the residue (5-50% EtOAc-hexanes) gave the title compound as a yellow solid (0.18 g). $^1$H NMR (400 MHz, CDCl$_3$): 9.04-9.03 (m, 1H), 8.55-8.52 (m, 1H), 8.30-8.27 (m, 1H), 7.64-7.60 (m, 1H), 7.38-7.31 (m, 3H), 7.12-7.07 (m, 1H), 6.38 (s, 1H), 3.74 (s, 8H).

Examples 38-43 were prepared in analogy with Example 37 using the specified benzamidine and Intermediate 2.

Example 38

4-(3-m-Tolyl-[1,2,4]thiadiazol-5-yl)-piperazine-1-carboxylic acid phenylamide

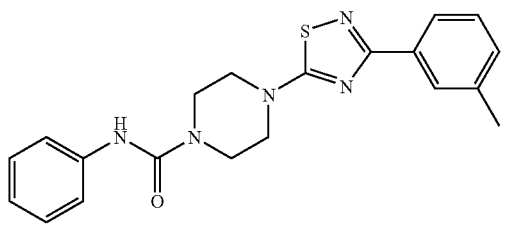

The title compound was prepared from 3-methyl-benzamidine hydrochloride. $^1$H NMR (400 MHz, CDCl$_3$): 8.01-7.98 (m, 2H), 7.37-7.30 (m, 5H), 7.25-7.22 (m, 1H), 7.11-7.06 (m, 1H), 6.34 (s, 1H), 3.70 (s, 8H).

Example 39

4-[3-(3,5-Dichloro-phenyl)-[1,2,4]thiadiazol-5-yl]-piperazine-1-carboxylic acid phenylamide

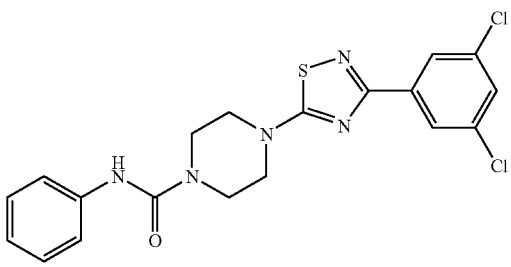

The title compound was prepared from 3,5-dichlorobenzamidine hydrochloride. $^1$H NMR (400 MHz, CDCl$_3$): 8.09 (d, J=2.0 Hz, 2H), 7.41-7.30 (m, 5H), 7.11-7.07 (m, 1H), 6.38 (s, 1H), 3.72 (s, 8H).

Example 40

4-(3-Furan-2-yl-[1,2,4]thiadiazol-5-yl)-piperazine-1-carboxylic acid phenylamide

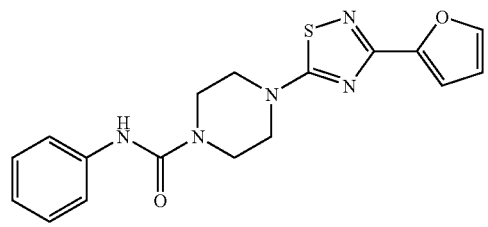

The title compound was prepared from furan-2-carboxamidine. $^1$H NMR (400 MHz, CDCl$_3$): 7.55-7.54 (m, 1H), 7.37-7.30 (m, 4H), 7.11-7.04 (m, 2H), 6.52-6.51 (m, 1H), 6.38 (s, 1H), 3.70 (s, 8H).

Example 41

4-(3-Furan-3-yl-[1,2,4]thiadiazol-5-yl)-piperazine-1-carboxylic acid phenylamide

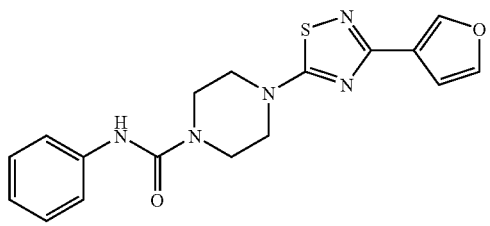

The title compound was prepared from furan-3-carboxamidine. $^1$H NMR (400 MHz, CDCl$_3$): 8.04-8.03 (m, 1H), 7.46-7.45 (m, 1H), 7.37-7.30 (m, 4H), 7.10-7.04 (m, 1H), 6.92-6.91 (m, 1H), 6.38 (s, 1H), 3.71-3.67 (m, 8H).

Example 42

4-(3-Thiophen-2-yl-[1,2,4]thiadiazol-5-yl)-piperazine-1-carboxylic acid phenylamide

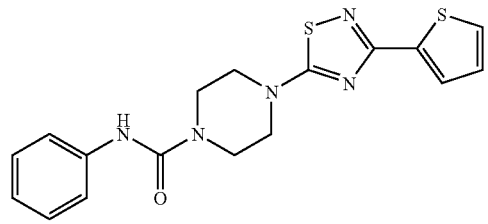

The title compound was prepared from thiophene-2-carboxamidine. $^1$H NMR (400 MHz, CDCl$_3$): 7.75-7.74 (m, 1H), 7.40-7.30 (m, 5H), 7.10-7.06 (m, 2H), 6.38 (s, 1H), 3.70 (s, 8H).

Example 43

4-(3-Thiophen-3-yl-[1,2,4]thiadiazol-5-yl)-piperazine-1-carboxylic acid phenylamide

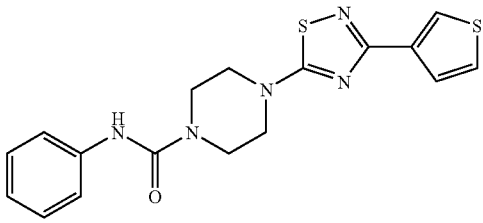

The title compound was prepared from thiophene-3-carboxamidine. $^1$H NMR (400 MHz, CDCl$_3$): 8.02-8.01 (m, 1H), 7.71-7.69 (m, 1H), 7.37-7.30 (m, 5H), 7.11-7.06 (m, 1H), 6.36 (s, 1H), 3.70 (s, 8H).

Example 44

4-(3-Morpholin-4-yl-[1,2,4]thiadiazol-5-yl)-piperazine-1-carboxylic acid phenylamide

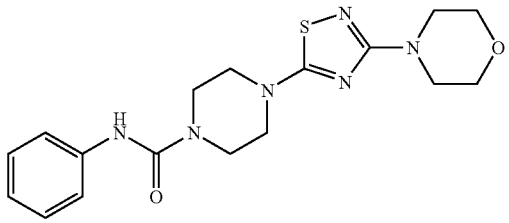

A solution of Intermediate 12 and morpholine (0.044 mL) in DMSO (0.5 mL) was heated at 120° C. for 20 h. The resulting mixture was cooled to rt, treated with water (10 mL), and extracted with EtOAc (20 mL). The organic extracts were dried (MgSO$_4$) and concentrated. Chromatography of the residue by preparative TLC (50% EtOAc-hexanes) gave the title compound as an ivory solid (45 mg). $^1$H NMR (400 MHz, CDCl$_3$): 7.36-7.28 (m, 4H), 7.08-7.04 (m, 1H), 6.30 (s, 1H), 3.77-3.74 (m, 6H), 3.67-3.54 (m, 6H), 3.50-3.47 (m, 4H).

Biological Testing:

Assay Method 1

T84 frozen pellets (contents of 1-4×15 cm culture dishes) were homogenized in 300 mL of FAAH assay buffer (125 mM Tris, 1 mM EDTA, 0.2% glycerol, 0.02% Triton X-100, 0.4 mM Hepes, pH 9). The assay mixture was prepared from 50 μL of the cell homogenate, 10 μL of the test compound, and 40 μL of anandamide [1-$^3$H-ethanolamine] ($^3$H-AEA; Perkin-Elmer, 10.3 C$_i$/mmol), which was added last, for a final tracer concentration of 200 nM. The reaction mixture was incubated at rt for 1 hour (h). During the incubation, 96-well Multiscreen filter plates (catalog number MAFC-NOB50; Millipore, Bedford, Mass. USA) were loaded with 25 μL of activated charcoal (Multiscreen column loader, catalog number MACL09625, Millipore) and washed once with 100 μL of MeOH. Also during the incubation, 96-well DYNEX MicroLite plates (catalog number NL510410) were loaded with 100 μL of MicroScint40 (catalog number 6013641, Packard Bioscience, Meriden, Conn., USA). After the 1 h incubation, 60 μL of the reaction mixture were transferred to the charcoal plates, which were then assembled on top of the DYNEX plates using Centrifuge Alignment Frames (catalog number MACF09604, Millipore). The unbound, labeled ethanolamine was centrifuged through to the bottom plate (5 min at 2000 rpm), which was preloaded with the scintillant, as described above. The plates were sealed and left at rt for 1 h before counting on a Hewlett Packard TopCount. Results for compounds tested in this assay are presented in Table 1.

TABLE 1

| Ex. | IC$_{50}$ (nM) |
|---|---|
| 1 | 81 |
| 2 | 30 |
| 3 | 60 |
| 4 | 90 |
| 5 | 140 |
| 6 | 160 |
| 7 | 190 |
| 8 | 200 |
| 9 | 230 |
| 10 | 270 |
| 11 | 780 |
| 12 | 800 |
| 13 | 1,300 |
| 14 | 2500 |
| 15 | 4,000 |
| 16 | 5000 |
| 17 | 6,000 |
| 18 | >10,000 |
| 19 | >10,000 |
| 20 | >10,000 |
| 21 | 25 |
| 22 | 440 |
| 23 | >10,000 |
| 24 | >10,000 |
| 26 | >10,000 |
| 30 | >10,000 |
| 33 | 28 |
| 34 | 440 |
| 35 | 11 |
| 36 | 430 |
| 37 | >10,000 |

Assay Method 2

A. Transfection of Cells with Human FAAH

A 10-cm tissue culture dish with a confluent monolayer of SK-N-MC cells was split 2 days (d) prior to transfection. Using sterile technique, the media was removed and the cells were detached from the dish by the addition of trypsin. One fifth of the cells were then placed onto a new 10-cm dish. Cells were grown in a 37° C. incubator with 5% CO$_2$ in Minimal Essential Media Eagle with 10% Fetal Bovine Serum. After 2 d, cells were approximately 80% confluent. These cells were removed from the dish with trypsin and pelleted in a clinical centrifuge. The pellet was re-suspended in 400 μL complete media and transferred to an electroporation cuvette with a 0.4 cm gap between the electrodes. Supercoiled human FMH cDNA (1 μg) was added to the cells and mixed. The voltage for the electroporation was set at 0.25 kV, and the capacitance was set at 960 μF. After electroporation, the cells were diluted into complete media (10 mL) and plated onto four 10-cm dishes. Because of the variability in the efficiency of electroporation, four different concentrations of cells were plated. The ratios used were 1:20, 1:10, and 1:5, with the remainder of the cells being added to the fourth dish. The cells were allowed to recover for 24 h before adding the selection media (complete media with 600 μg/mL G418). After 10 d, dishes were analyzed for surviving colonies of cells. Dishes with well-isolated colonies were used. Cells from individual colonies were isolated and tested. The clones that showed the most FAAH activity, as measured by anandamide hydrolysis, were used for further study.

B. FAAH Assay

T84 frozen cell pellets or transfected SK-N-MC cells (contents of 1×15 cm culture dishes) were homogenized in 50 mL of FAAH assay buffer (125 mM Tris, 1 mM EDTA, 0.2% Glycerol, 0.02% Triton X-100, 0.4 mM Hepes, pH 9). The assay mixture consisted of 50 μL of the cell homogenate, 10 μL of the test compound, and 40 μL of anandamide [1-$^3$H-ethanolamine] ($^3$H-AEA, Perkin-Elmer, 10.3 C$_i$/mmol), which was added last, for a final tracer concentration of 80 nM. The reaction mixture was incubated at rt for 1 h. During the incubation, 96-well Multiscreen filter plates (catalog number MAFCNOB50; Millipore, Bedford, Me., USA) were loaded with 25 μL of activated charcoal (Multiscreen column loader, catalog number MACL09625, Millipore) and washed once with 100 μL of MeOH. Also during the incubation, 96-well DYNEX MicroLite plates (catalog number NL510410) were loaded with 100 μL of MicroScint40 (catalog number 6013641, Packard Bioscience, Meriden, Conn., USA). After the 1 h incubation, 60 μL of the reaction mixture were transferred to the charcoal plates, which were then assembled on top of the DYNEX plates using Centrifuge Alignment Frames (catalog number MACF09604, Millipore). The unbound labeled ethanolamine was centrifuged through to the bottom plate (5 min at 2000 rpm), which was preloaded with the scintillant, as described above. The plates were sealed and left at rt for 1 h before counting on a Hewlett Packard TopCount. Results for compounds tested in this assay are presented in Table 2.

TABLE 2

| Ex. | IC$_{50}$ (nM) |
|---|---|
| 18 | >10,000 |
| 19 | >10,000 |
| 20 | >10,000 |
| 21 | 19 |
| 23 | >10,000 |
| 24 | >10,000 |
| 25 | >10,000 |
| 26 | >10,000 |
| 27 | 260 |
| 28 | 3,000 |
| 29 | >10,000 |
| 30 | >10,000 |
| 31 | 160 |
| 32 | 450 |
| 37 | >10,000 |
| 38 | 43 |
| 39 | 60 |
| 40 | 540 |
| 41 | 350 |
| 42 | 60 |
| 43 | 130 |
| 44 | >10,000 |

Assay Method 3

A. Transfection of Cells with Rat FAAH

A 10-cm tissue culture dish with a confluent monolayer of SK-N-MC cells was split 2 days (d) prior to transfection. Using sterile technique, the media was removed and the cells were detached from the dish by the addition of trypsin. One fifth of the cells were then placed onto a new 10-cm dish. Cells were grown in a 37° C. incubator with 5% CO$_2$ in Minimal Essential Media Eagle with 10% Fetal Bovine Serum. After 2 d, cells were approximately 80% confluent. These cells were removed from the dish with trypsin and pelleted in a clinical centrifuge. The pellet was re-suspended in 400 μL complete media and transferred to an electroporation cuvette with a 0.4 cm gap between the electrodes. Supercoiled rat FMH cDNA (1 μg) was added to the cells and mixed. The voltage for the electroporation was set at 0.25 kV, and the capacitance was set at 960 μF. After electroporation, the cells were diluted into complete media (10 mL) and plated onto four 10-cm dishes. Because of the variability in the efficiency of electroporation, four different concentrations of cells were plated. The ratios used were 1:20, 1:10, and 1:5, with the remainder of the cells being added to the fourth dish. The cells were allowed to recover for 24 h before adding the selection media (complete media with 600 μg/mL G418). After 10 d, dishes were analyzed for surviving colonies of cells. Dishes with well-isolated colonies were used. Cells from individual colonies were isolated and tested. The clones that showed the most FAAH activity, as measured by anandamide hydrolysis, were used for further study.

B. FAAH Assay

T84 frozen cell pellets or transfected SK-N-MC cells (contents of 1×15 cm culture dishes) were homogenized in 50 mL of FMH assay buffer (125 mM Tris, 1 mM EDTA, 0.2% Glycerol, 0.02% Triton X-100, 0.4 mM Hepes, pH 9). The assay mixture consisted of 50 μL of the cell homogenate, 10 μL of the test compound, and 40 μL of anandamide [1-$^3$H-ethanolamine] ($^3$H-AEA, Perkin-Elmer, 10.3 C$_i$/mmol), which was added last, for a final tracer concentration of 80 nM. The reaction mixture was incubated at rt for 1 h. During the incubation, 96-well Multiscreen filter plates (catalog number MAFCNOB50: Millipore, Bedford, Mass., USA) were loaded with 25 μL of activated charcoal (Multiscreen column loader, catalog number MACL09625, Millipore) and washed once with 100 μL of MeOH. Also during the incubation, 96-well DYNEX MicroLite plates (catalog number NL510410) were loaded with 100 μL of MicroScint40 (catalog number 60136411, Packard Bioscience, Meriden, Conn., USA). After the 1 h incubation, 60 μL of the reaction mixture were transferred to the charcoal plates, which were then assembled on top of the DYNEX plates using Centrifuge Alignment Frames (catalog number MACF09604, Millipore). The unbound labeled ethanolamine was centrifuged through to the bottom plate (5 min at 2000 rpm), which was preloaded with the scintillant, as described above. The plates were sealed and left at rt for 1 h before counting on a Hewlett Packard TopCount. Results for compounds tested in this assay are presented in Table 3.

TABLE 3

| Ex. | IC$_{50}$ (nM) |
|---|---|
| 1 | 46 |
| 18 | 250 |
| 19 | 490 |
| 20 | 350 |
| 21 | 6 |
| 23 | >10,000 |
| 24 | >10,000 |
| 25 | >10,000 |
| 26 | >10,000 |
| 27 | 1,100 |

TABLE 3-continued

| Ex. | IC$_{50}$ (nM) |
| --- | --- |
| 28 | 5,000 |
| 29 | 5,000 |
| 30 | >10,000 |
| 31 | 30 |
| 32 | 77 |
| 33 | 18 |
| 34 | 440 |
| 35 | 8 |
| 37 | >10,000 |
| 38 | 84 |
| 39 | 57 |
| 40 | 2,000 |
| 41 | 590 |
| 42 | 300 |
| 43 | 120 |
| 44 | >10,000 |

While the invention has been illustrated by reference to exemplary and preferred embodiments, it will be understood that the invention is intended not to be limited to the foregoing detailed description, but to be defined by the appended claims as properly construed under principles of patent law.

What is claimed is:

1. A compound of Formula (I):

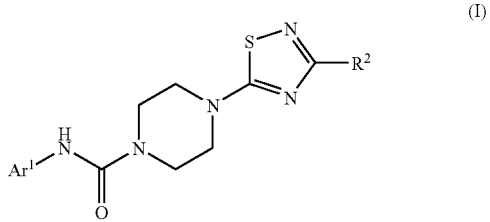

(I)

wherein:
Ar$^1$ is a pyridyl, pyrimidinyl, thiazolyl, oxazolyl, naphthyl, or phenyl group, unsubstituted or substituted at a carbon ring member with one or two R$^a$ moieties;
where each R$^a$ moiety is independently selected from the group consisting of —C$_{1-4}$alkyl, —C$_{3-7}$cycloalkyl, phenyl, benzyloxy, —C$_{2-4}$alkenyl, —NO$_2$, —CN, —OH, —OC$_{1-4}$alkyl, fluoro, chloro, bromo, iodo, —CF$_3$, —SH, —SC$_{1-4}$alkyl, —SO$_2$C$_{1-4}$alkyl, —SOC$_{1-4}$alkyl, —CO$_2$C$_{1-4}$alkyl, —CO$_2$H, —COC$_{1-4}$ alkyl, —SO$_2$NR$^b$R$^c$, —NR$^b$SO$_2$R$^c$, —C(=O)NR$^b$R$^c$, —NR$^b$C(=O)R$^c$, and —N(R$^b$)R$^c$, where R$^b$ and R$^c$ are each independently —H or —C$_{1-4}$ alkyl, or R$^b$ and R$^c$ are taken together to form a 4- to 7-membered heterocycloalkyl ring; and
R$^2$ is R$^3$, R$^4$, or Ar$^2$,
where R$^3$ is a —N-piperidinyl, —N-piperazinyl, —N-morpholinyl, —N-thiomorpholinyl, —N-dioxo-1λ$^6$-thiomorpholinyl, or —N-pyrrolidinyl group, unsubstituted or substituted with one or two R$^d$ moieties;
where each R$^d$ moiety is independently selected from the group consisting of —C$_{1-4}$alkyl, —C$_{3-7}$cycloalkyl, phenyl, —OH, and —C$_{2-4}$alkenyl;
R$^4$ is —NR$^e$R$^f$, wherein R$^e$ and R$^f$ are each independently —H, —C$_{1-4}$alkyl, or —C$_{3-7}$cycloalkyl; and
Ar$^2$ is a phenyl, thiophenyl, furanyl, pyridyl, pyrimidinyl, or pyrazinyl group, unsubstituted or substituted at a carbon ring member with one or two R$^g$ moieties;
where each R$^g$ moiety is independently selected from the group consisting of —C$_{1-4}$alkyl, —C$_{3-7}$cycloalkyl, phenyl, —C$_{2-4}$alkenyl, —NO$_2$, —CN, —OC$_{1-4}$alkyl, fluoro, chloro, bromo, iodo, —CF$_3$, —OCF$_3$, —SCF$_3$, —SC$_{1-4}$alkyl, —SO$_2$C$_{1-4}$alkyl, —SOC$_{1-4}$alkyl, —CO$_2$C$_{1-4}$alkyl, —COC$_{1-4}$alkyl, —SO$_2$NR$^h$R$^i$, —NR$^h$SO$_2$R$^i$, —C(=O)NR$^h$R$^i$, —NR$^b$C(=O)R$^c$, and —N(R$^h$)R$^i$, where R$^h$ and R$^i$ are each independently —H or —C$_{1-4}$alkyl or R$^b$ and R$^c$ are taken together to form a 4- to 7-membered heterocycloalkyl ring; and
further wherein Ar$^1$ and R$^2$ are not both unsubstituted phenyl;
or a pharmaceutically acceptable salt or pharmaceutically acceptable prodrug of such compound.

2. A compound, pharmaceutically acceptable salt or pharmaceutically acceptable prodrug as defined in claim 1, wherein Ar$^1$ is a phenyl, 2-naphthyl, 2-pyridyl, 3-pyridyl, 4-pyridyl, 2-pyrimidinyl, or 2-thiazolyl group, unsubstituted or substituted at a carbon ring atom with one or two R$^a$ moieties as previously defined.

3. A compound, pharmaceutically acceptable salt or pharmaceutically acceptable prodrug as defined in claim 1, wherein Ar$^1$ is a phenyl group unsubstituted or substituted at a carbon ring atom with one or two R$^a$ moieties as previously defined.

4. A compound, pharmaceutically acceptable salt or pharmaceutically acceptable prodrug as defined in claim 1, wherein Ar$^1$ is 2-chlorophenyl, 3-fluorophenyl, 4-fluorophenyl, 4-methoxyphenyl, 4-benzyloxyphenyl, 3-methylphenyl, 2-nitrophenyl, 2-methoxyphenyl, 3-chlorophenyl, 4-methylphenyl, 2-methylphenyl, 3-methoxyphenyl, 2-methylsulfanylphenyl, 4-biphenyl, 4-ethoxyphenyl, 2-fluorophenyl, 4-chlorophenyl, 2-isopropylphenyl, 2-trifluoromethyl, 4-nitrophenyl, 4-dimethylaminophenyl, 4-carbomethoxyphenyl, naphthyl, 2-pyridyl, 3-pyridyl, 4-pyridyl, 2-pyrimidinyl, 2-naphthyl, 2-thiazolyl, or phenyl.

5. A compound as defined in claim 4, wherein R$^2$ is —N-piperidinyl, 4-methyl-N-piperidinyl, —N-piperazinyl, —N-morpholinyl, —N-pyrrolidinyl, 4-methylphenyl, 4-methoxyphenyl, 4-chlorophenyl, 4-fluorophenyl, 3,5-dichlorophenyl, 3-nitrophenyl, 3-methylphenyl, 3-furanyl, thiophen-2-yl, thiophen-3-yl, or phenyl.

6. A compound as defined in claim 4, wherein R$^2$ is a phenyl group, unsubstituted or mono- or di-substituted with fluoro or chloro.

7. A compound as defined in claim 4, wherein R$^2$ is 2-furanyl, 3-furanyl, thiophen-2-yl, or thiophen-3-yl.

8. A compound, pharmaceutically acceptable salt or pharmaceutically acceptable prodrug as defined in claim 1, wherein Ar$^1$ is a phenyl group unsubstituted or substituted with fluoro or chloro.

9. A compound, pharmaceutically acceptable salt or pharmaceutically acceptable prodrug as defined in claim 1, wherein Ar$^1$ is 2-pyrimidinyl, 2-thiazolyl, 2-pyridyl, 3-pyridyl, or 4-pyridyl.

10. A compound, pharmaceutically acceptable salt or pharmaceutically acceptable prodrug as defined in claim 1, wherein R$^2$ is a —N-piperidinyl, —N-piperazinyl, —N-morpholinyl, or N-pyrrolidinyl group, unsubstituted or substituted at a carbon ring atom with one or two R$^d$ moieties as previously defined.

11. A compound, pharmaceutically acceptable salt or pharmaceutically acceptable prodrug as defined in claim 1, wherein R$^2$ is —N-piperidinyl, 4-methyl-N-piperidinyl, —N-piperazinyl, —N-morpholinyl, or N-pyrrolidinyl.

12. A compound, pharmaceutically acceptable salt or pharmaceutically acceptable prodrug as defined in claim 1, wherein R² is a phenyl, 3-furanyl, thiophen-2-yl, or thiophen-3-yl group, unsubstituted or substituted at a carbon ring atom with one or two R$^g$ moieties as previously defined.

13. A compound as defined in claim 1, wherein R² is —N-piperidinyl, 4-methyl-N-piperidinyl, —N-piperazinyl, —N-morpholinyl, —N-pyrrolidinyl, 4-methylphenyl, 4-methoxyphenyl, 4-chlorophenyl, 4-fluorophenyl, 3,5-dichlorophenyl, 3-nitrophenyl, 3-methylphenyl, 3-furanyl, thiophen-2-yl, thiophen-3-yl, or phenyl.

14. A compound selected from the group consisting of:
- 4-(3-phenyl-[1,2,4]thiadiazol-5-yl)-piperazine-1-carboxylic acid (2-chloro-phenyl)-amide;
- 4-(3-phenyl-[1,2,4]thiadiazol-5-yl)-piperazine-1-carboxylic acid (3-fluoro-phenyl)-amide;
- 4-(3-phenyl-[1,2,4]thiadiazol-5-yl)-piperazine-1-carboxylic acid (4-fluoro-phenyl)-amide;
- 4-(3-phenyl-[1,2,4]thiadiazol-5-yl)-piperazine-1-carboxylic acid (4-methoxy-phenyl)-amide;
- 4-(3-phenyl-[1,2,4]thiadiazol-5-yl)-piperazine-1-carboxylic acid (4-benzyloxy-phenyl)-amide;
- 4-(3-phenyl-[1,2,4]thiadiazol-5-yl)-piperazine-1-carboxylic acid m-tolylamide;
- 4-(3-phenyl-[1,2,4]thiadiazol-5-yl)-piperazine-1-carboxylic acid (2-nitro-phenyl)-amide;
- 4-(3-phenyl-[1,2,4]thiadiazol-5-yl)-piperazine-1-carboxylic acid (2-methoxy-phenyl)-amide;
- 4-(3-phenyl-[1,2,4]thiadiazol-5-yl)-piperazine-1-carboxylic acid (3-chloro-phenyl)-amide;
- 4-(3-phenyl-[1,2,4]thiadiazol-5-yl)-piperazine-1-carboxylic acid p-tolylamide;
- 4-(3-phenyl-[1,2,4]thiadiazol-5-yl)-piperazine-1-carboxylic acid o-tolylamide;
- 4-(3-phenyl-[1,2,4]thiadiazol-5-yl)-piperazine-1-carboxylic acid (2-methylsulfanyl-phenyl)-amide;
- 4-(3-phenyl-[1,2,4]thiadiazol-5-yl)-piperazine-1-carboxylic acid (3-methoxy-phenyl)-amide;
- 4-(3-phenyl-[1,2,4]thiadiazol-5-yl)-piperazine-1-carboxylic acid biphenyl-4-ylamide;
- 4-(3-phenyl-[1,2,4]thiadiazol-5-yl)-piperazine-1-carboxylic acid naphthalen-2-ylamide;
- 4-(3-phenyl-[1,2,4]thiadiazol-5-yl)-piperazine-1-carboxylic acid (4-ethoxy-phenyl)-amide;
- 4-(3-p-tolyl-[1,2,4]thiadiazol-5-yl)-piperazine-1-carboxylic acid phenylamide;
- 4-[3-(4-methoxy-phenyl)-[1,2,4]thiadiazol-5-yl]-piperazine-1-carboxylic acid phenylamide;
- 4-[3-(4-chloro-phenyl)-[1,2,4]thiadiazol-5-yl]-piperazine-1-carboxylic acid phenylamide;
- 4-(3-phenyl-[1,2,4]thiadiazol-5-yl)-piperazine-1-carboxylic acid (2-fluoro-phenyl)-amide;
- 4-(3-phenyl-[1,2,4]thiadiazol-5-yl)-piperazine-1-carboxylic acid (4-chloro-phenyl)-amide;
- 4-(3-phenyl-[1,2,4]thiadiazol-5-yl)-piperazine-1-carboxylic acid (2-isopropyl-phenyl)-amide;
- 4-(3-phenyl-[1,2,4]thiadiazol-5-yl)-piperazine-1-carboxylic acid (2-trifluoromethyl-phenyl)-amide;
- 4-(3-phenyl-[1,2,4]thiadiazol-5-yl)-piperazine-1-carboxylic acid (4-nitro-phenyl)-amide;
- 4-(3-phenyl-[1,2,4]thiadiazol-5-yl)-piperazine-1-carboxylic acid (4-dimethylamino-phenyl)-amide;
- 4-(3-piperidin-1-yl-[1,2,4]thiadiazol-5-yl)-piperazine-1-carboxylic acid phenylamide;
- 4-(3-pyrrolidin-1-yl-[1,2,4]thiadiazol-5-yl)-piperazine-1-carboxylic acid phenylamide;
- 4-[3-(4-methyl-piperidin-1-yl)-[1,2,4]thiadiazol-5-yl]-piperazine-1-carboxylic acid phenylamide;
- 4-{[4-(3-phenyl-[1,2,4]thiadiazol-5-yl)-piperazine-1-carbonyl]-amino}-benzoic acid methyl ester;
- 4-(3-phenyl-[1,2,4]thiadiazol-5-yl)-piperazine-1-carboxylic acid pyrimidin-2-ylamide;
- 4-(3-phenyl-[1,2,4]thiadiazol-5-yl)-piperazine-1-carboxylic acid thiazol-2-ylamide;
- 4-(3-phenyl-[1,2,4]thiadiazol-5-yl)-piperazine-1-carboxylic acid pyridin-4-ylamide;
- 4-(3-phenyl-[1,2,4]thiadiazol-5-yl)-piperazine-1-carboxylic acid pyridin-2-ylamide;
- 4-(3-phenyl-[1,2,4]thiadiazol-5-yl)-piperazine-1-carboxylic acid pyridin-3-ylamide;
- 4-[3-(4-fluoro-phenyl)-[1,2,4]thiadiazol-5-yl]-piperazine-1-carboxylic acid phenylamide;
- 4-[3-(3-nitro-phenyl)-[1,2,4]thiadiazol-5-yl]-piperazine-1-carboxylic acid phenylamide;
- 4-(3-m-tolyl-[1,2,4]thiadiazol-5-yl)-piperazine-1-carboxylic acid phenylamide;
- 4-[3-(3,5-dichloro-phenyl)-[1,2,4]thiadiazol-5-yl]-piperazine-1-carboxylic acid phenylamide;
- 4-(3-furan-2-yl-[1,2,4]thiadiazol-5-yl)-piperazine-1-carboxylic acid phenylamide;
- 4-(3-furan-3-yl-[1,2,4]thiadiazol-5-yl)-piperazine-1-carboxylic acid phenylamide;
- 4-(3-thiophen-2-yl-[1,2,4]thiadiazol-5-yl)-piperazine-1-carboxylic acid phenylamide;
- 4-(3-thiophen-3-yl-[1,2,4]thiadiazol-5-yl)-piperazine-1-carboxylic acid phenylamide; and
- 4-(3-morpholin-4-yl-[1,2,4]thiadiazol-5-yl)-piperazine-1-carboxylic acid phenylamide;

and pharmaceutically acceptable salts thereof.

15. A compound or pharmaceutically acceptable salt according to claim 1.

16. A pharmaceutical composition for treating a disease, disorder, or medical condition mediated by FAAH activity, comprising:

(a) an effective amount of an agent selected from the group consisting of compounds of Formula (I):

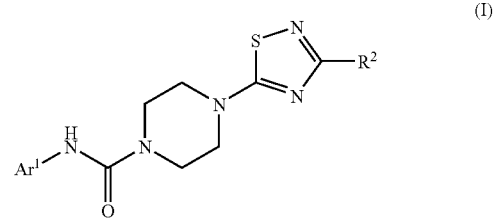

wherein:
Ar¹ is a pyridyl, pyrimidinyl, thiazolyl, oxazolyl, naphthyl, or phenyl group, unsubstituted or substituted at a carbon ring member with one or two R$^a$ moieties;
where each R$^a$ moiety is independently selected from the group consisting of —C$_{1-4}$alkyl, —C$_{3-7}$cycloalkyl, phenyl, benzyloxy, —C$_{2-4}$alkenyl, —NO$_2$, —CN, —OH, —OC$_{1-4}$alkyl, fluoro, chloro, bromo, iodo, —CF$_3$, —OCF$_3$, —SCF$_3$, —SH, —SC$_{1-4}$alkyl, —SO$_2$C$_{1-4}$alkyl, —SOC$_{1-4}$alkyl, —CO$_2$C$_{1-4}$alkyl, —CO$_2$H, —COC$_{1-4}$alkyl, —SO$_2$NR$^b$R$^c$, —NR$^b$SO$_2$R$^c$, —C(=O)NR$^b$R$^c$, —NR$^b$C(=O)R$^c$, and —N(R$^b$)R$^c$, where R$^b$ and R$^c$ are each independently —H or —C$_{1-4}$alkyl, or R$^b$ and R$^c$ are taken together to form a 4- to 7-membered heterocycloalkyl ring; and R² is R³, R⁴, or Ar²,
where R³ is a —N-piperidinyl, —N-piperazinyl, —N-morpholinyl, —N-thiomorpholinyl, —N-dioxo-1λ⁶-thiomorpholinyl, or —N-pyrrolidinyl group, unsubstituted or substituted with one or two R$^d$ moieties;
where each R$^d$ moiety is independently selected from the group consisting of —C$_{1-4}$alkyl, —C$_{3-7}$cycloalkyl, phenyl, —OH, and —C$_{2-4}$alkenyl;
R⁴ is —NR$^e$R$^f$, wherein R$^e$ and R$^f$ are each independently —H, —C$_{1-4}$alkyl, or —C$_{3-7}$cycloalkyl; and
Ar² is a phenyl, thiophenyl, furanyl, pyridyl, pyrimidinyl, or pyrazinyl group, unsubstituted or substituted at a carbon ring member with one or two R$^g$ moieties;
where each R$^g$ moiety is independently selected from the group consisting of —C$_{1-4}$alkyl, —C$_3$cycloalkyl, phenyl, —C$_{2-4}$alkenyl, —NO$_2$, —CN, —OC$_{1-4}$alkyl, fluoro, chloro, bromo, iodo, —CF$_3$, —OCF$_3$, —SCF$_3$, —SC$_{1-4}$alkyl, —SO$_2$C$_{1-4}$alkyl, —SOC$_{1-4}$alkyl, —CO$_2$C$_{1-4}$alkyl, —COC$_{1-4}$alkyl, —SO$_2$NR$^h$R$^i$, —NR$^h$SO$_2$R$^i$, —C(═O)NR$^h$R$^i$, —NR$^b$C(═O)R$^c$, and —N(R$^h$)R$^i$, where R$^h$ and R$^i$ are each independently —H or —C$_{1-4}$alkyl, or R$^b$ and R$^c$ are taken together to form a 4- to 7-membered heterocycloalkyl ring;
and pharmaceutically acceptable salts or pharmaceutically acceptable prodrugs thereof; and
(b) a pharmaceutically acceptable excipient.

17. A pharmaceutical composition according to claim 16, wherein said agent is selected from the group consisting of:
4-(3-phenyl-[1,2,4]thiadiazol-5-yl)-piperazine-1-carboxylic acid phenylamide;
4-(3-phenyl-[1,2,4]thiadiazol-5-yl)-piperazine-1-carboxylic acid (2-chloro-phenyl)-amide;
4-(3-phenyl-[1,2,4]thiadiazol-5-yl)-piperazine-1-carboxylic acid (3-fluoro-phenyl)-amide;
4-(3-phenyl-[1,2,4]thiadiazol-5-yl)-piperazine-1-carboxylic acid (4-fluoro-phenyl)-amide;
4-(3-phenyl-[1,2,4]thiadiazol-5-yl)-piperazine-1-carboxylic acid (4-methoxy-phenyl)-amide;
4-(3-phenyl-[1,2,4]thiadiazol-5-yl)-piperazine-1-carboxylic acid (4-benzyloxy-phenyl)-amide;
4-(3-phenyl-[1,2,4]thiadiazol-5-yl)-piperazine-1-carboxylic acid m-tolylamide;
4-(3-phenyl-[1,2,4]thiadiazol-5-yl)-piperazine-1-carboxylic acid (2-nitro-phenyl)-amide;
4-(3-phenyl-[1,2,4]thiadiazol-5-yl)-piperazine-1-carboxylic acid (2-methoxy-phenyl)-amide;
4-(3-phenyl-[1,2,4]thiadiazol-5-yl)-piperazine-1-carboxylic acid (3-chloro-phenyl)-amide;
4-(3-phenyl-[1,2,4]thiadiazol-5-yl)-piperazine-1-carboxylic acid p-tolylamide;
4-(3-phenyl-[1,2,4]thiadiazol-5-yl)-piperazine-1-carboxylic acid o-tolylamide;
4-(3-phenyl-[1,2,4]thiadiazol-5-yl)-piperazine-1-carboxylic acid (2-methylsulfanyl-phenyl)-amide;
4-(3-phenyl-[1,2,4]thiadiazol-5-yl)-piperazine-1-carboxylic acid (3-methoxy-phenyl)-amide;
4-(3-phenyl-[1,2,4]thiadiazol-5-yl)-piperazine-1-carboxylic acid biphenyl-4-ylamide;
4-(3-phenyl-[1,2,4]thiadiazol-5-yl)-piperazine-1-carboxylic acid naphthalen-2-ylamide;
4-(3-phenyl-[1,2,4]thiadiazol-5-yl)-piperazine-1-carboxylic acid (4-ethoxy-phenyl)-amide;
4-(3-p-tolyl-[1,2,4]thiadiazol-5-yl)-piperazine-1-carboxylic acid phenylamide;
4-[3-(4-methoxy-phenyl)-[1,2,4]thiadiazol-5-yl]-piperazine-1-carboxylic acid phenylamide;
4-[3-(4-chloro-phenyl)-[1,2,4]thiadiazol-5-yl]-piperazine-1-carboxylic acid phenylamide;
4-(3-phenyl-[1,2,4]thiadiazol-5-yl)-piperazine-1-carboxylic acid (2-fluoro-phenyl)-amide;
4-(3-phenyl-[1,2,4]thiadiazol-5-yl)-piperazine-1-carboxylic acid (4-chloro-phenyl)-amide;
4-(3-phenyl-[1,2,4]thiadiazol-5-yl)-piperazine-1-carboxylic acid (2-isopropyl-phenyl)-amide;
4-(3-phenyl-[1,2,4]thiadiazol-5-yl)-piperazine-1-carboxylic acid (2-trifluoromethyl-phenyl)-amide;
4-(3-phenyl-[1,2,4]thiadiazol-5-yl)-piperazine-1-carboxylic acid (4-nitro-phenyl)-amide;
4-(3-phenyl-[1,2,4]thiadiazol-5-yl)-piperazine-1-carboxylic acid (4-dimethylamino-phenyl)-amide;
4-(3-piperidin-1-yl-[1,2,4]thiadiazol-5-yl)-piperazine-1-carboxylic acid phenylamide;
4-(3-pyrrolidin-1-yl-[1,2,4]thiadiazol-5-yl)-piperazine-1-carboxylic acid phenylamide;
4-[3-(4-methyl-piperidin-1-yl)-[1,2,4]thiadiazol-5-yl]-piperazine-1-carboxylic acid phenylamide;
4-{[4-(3-phenyl-[1,2,4]thiadiazol-5-yl)-piperazine-1-carbonyl]-amino}-benzoic acid methyl ester;
4-(3-phenyl-[1,2,4]thiadiazol-5-yl)-piperazine-1-carboxylic acid pyrimidin-2-ylamide;
4-(3-phenyl-[1,2,4]thiadiazol-5-yl)-piperazine-1-carboxylic acid thiazol-2-ylamide;
4-(3-phenyl-[1,2,4]thiadiazol-5-yl)-piperazine-1-carboxylic acid pyridin-4-ylamide;
4-(3-phenyl-[1,2,4]thiadiazol-5-yl)-piperazine-1-carboxylic acid pyridin-2-ylamide;
4-(3-phenyl-[1,2,4]thiadiazol-5-yl)-piperazine-1-carboxylic acid pyridin-3-ylamide;
4-[3-(4-fluoro-phenyl)-[1,2,4]thiadiazol-5-yl]-piperazine-1-carboxylic acid phenylamide;
4-[3-(3-nitro-phenyl)-[1,2,4]thiadiazol-5-yl]-piperazine-1-carboxylic acid phenylamide;
4-(3-m-tolyl-[1,2,4]thiadiazol-5-yl)-piperazine-1-carboxylic acid phenylamide;
4-[3-(3,5-dichloro-phenyl)-[1,2,4]thiadiazol-5-yl]-piperazine-1-carboxylic acid phenylamide;
4-(3-furan-2-yl-[1,2,4]thiadiazol-5-yl)-piperazine-1-carboxylic acid phenylamide;
4-(3-furan-3-yl-[1,2,4]thiadiazol-5-yl)-piperazine-1-carboxylic acid phenylamide;
4-(3-thiophen-2-yl-[1,2,4]thiadiazol-5-yl)-piperazine-1-carboxylic acid phenylamide;
4-(3-thiophen-3-yl-[1,2,4]thiadiazol-5-yl)-piperazine-1-carboxylic acid phenylamide; and
4-(3-morpholin-4-yl-[1,2,4]thiadiazol-5-yl)-piperazine-1-carboxylic acid phenylamide;
and pharmaceutically acceptable salts thereof.

18. A pharmaceutical composition according to claim 16, further comprising: an analgesic selected from the group consisting of opioids and non-steroidal anti-inflammatory drugs.

19. A pharmaceutical composition according to claim 16, further comprising: an additional active ingredient selected from the group consisting of aspirin, acetaminophen, opioids, ibuprofen, naproxen, COX-2 inhibitors, gabapentin, pregabalin, and tramadol.

20. A method of treating a subject suffering from or diagnosed with pain, comprising administering to the subject in need of such treatment an effective amount of a compound of Formula (I):

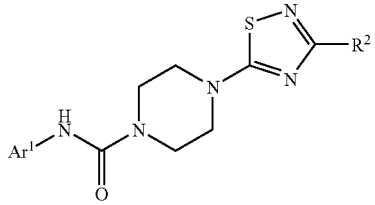

(I)

wherein:
Ar¹ is a pyridyl, pyrimidinyl, thiazolyl, oxazolyl, naphthyl, or phenyl group, unsubstituted or substituted at a carbon ring member with one or two $R^a$ moieties;
  where each $R^a$ moiety is independently selected from the group consisting of —$C_{1-4}$alkyl, —$C_{3-7}$cycloalkyl, phenyl, benzyloxy, —$C_{2-4}$alkenyl, —$NO_2$, —CN, —OH, —$OC_{1-4}$alkyl, fluoro, chloro, bromo, iodo, —$CF_3$, —$OCF_3$, —$SCF_3$, —SH, —$SC_{1-4}$alkyl, —$SO_2C_{1-4}$alkyl, —$SOC_{1-4}$alkyl, —$CO_2C_{1-4}$alkyl, —$CO_2H$, —$COC_{1-4}$alkyl, —$SO_2NR^bR^c$, —$NR^bSO_2R^c$, —$C(=O)NR^bR^c$, —$NR^bC(=O)R^c$, and —$N(R^b)R^c$, where $R^b$ and $R^c$ are each independently —H or —$C_{1-4}$alkyl, or $R^b$ and $R^c$ are taken together to form a 4- to 7-membered heterocycloalkyl ring; and
$R^2$ is $R^3$, $R^4$, or $Ar^2$,
  where $R^3$ is a —N-piperidinyl, —N-piperazinyl, —N-morpholinyl, —N-thiomorpholinyl, —N-dioxo-1$\lambda^6$-thiomorpholinyl, or —N-pyrrolidinyl group, unsubstituted or substituted with one or two $R^d$ moieties;
    where each $R^d$ moiety is independently selected from the group consisting of —$C_{1-4}$alkyl, —$C_{3-7}$cycloalkyl, phenyl, —OH, and —$C_{2-4}$alkenyl;
  $R^4$ is —$NR^eR^f$, wherein $R^e$ and $R^f$ are each independently —H, —$C_{1-4}$alkyl, or —$C_{1-3}$cycloalkyl; and
  $Ar^2$ is a phenyl, thiophenyl, furanyl, pyridyl, pyrimidinyl, or pyrazinyl group, unsubstituted or substituted at a carbon ring member with one or two $R^g$ moieties;
    where each $R^g$ moiety is independently selected from the group consisting of —$C_{1-4}$alkyl, —$C_{3-7}$cycloalkyl, phenyl, —$C_{2-4}$alkenyl, —$NO_2$, —CN, —$OC_{1-4}$alkyl, fluoro, chloro, bromo, iodo, —$CF_3$, —$OCF_3$, —$SCF_3$, —$SC_{1-4}$alkyl, —$SO_2C_{1-4}$alkyl, —$SOC_{1-4}$alkyl, —$CO_2C_{1-4}$alkyl, —$COC_{1-4}$alkyl, —$SO_2NR^hR^i$, —$NR^hSO_2R^i$, —$C(=O)NR^hR^i$, —$NR^hC(=O)R^c$, and —$N(R^h)R^i$, where $R^h$ and $R^i$ are each independently —H or —$C_{1-4}$alkyl, or $R^b$ and $R^c$ are taken together to form a 4- to 7-membered heterocycloalkyl ring;
or a pharmaceutically acceptable salt or pharmaceutically acceptable prodrug of such compound.

21. A method according to claim 20, wherein said compound is selected from the group consisting of:
  4-(3-phenyl-[1,2,4]thiadiazol-5-yl)-piperazine-1-carboxylic acid phenylamide;
  4-(3-phenyl-[1,2,4]thiadiazol-5-yl)-piperazine-1-carboxylic acid (2-chloro-phenyl)-amide;
  4-(3-phenyl-[1,2,4]thiadiazol-5-yl)-piperazine-1-carboxylic acid (3-fluoro-phenyl)-amide;
  4-(3-phenyl-[1,2,4]thiadiazol-5-yl)-piperazine-1-carboxylic acid (4-fluoro-phenyl)-amide;
  4-(3-phenyl-[1,2,4]thiadiazol-5-yl)-piperazine-1-carboxylic acid (4-methoxy-phenyl)-amide;
  4-(3-phenyl-[1,2,4]thiadiazol-5-yl)-piperazine-1-carboxylic acid (4-benzyloxy-phenyl)-amide;
  4-(3-phenyl-[1,2,4]thiadiazol-5-yl)-piperazine-1-carboxylic acid m-tolylamide;
  4-(3-phenyl-[1,2,4]thiadiazol-5-yl)-piperazine-1-carboxylic acid (2-nitro-phenyl)-amide;
  4-(3-phenyl-[1,2,4]thiadiazol-5-yl)-piperazine-1-carboxylic acid (2-methoxy-phenyl)-amide;
  4-(3-phenyl-[1,2,4]thiadiazol-5-yl)-piperazine-1-carboxylic acid (3-chloro-phenyl)-amide;
  4-(3-phenyl-[1,2,4]thiadiazol-5-yl)-piperazine-1-carboxylic acid p-tolylamide;
  4-(3-phenyl-[1,2,4]thiadiazol-5-yl)-piperazine-1-carboxylic acid o-tolylamide;
  4-(3-phenyl-[1,2,4]thiadiazol-5-yl)-piperazine-1-carboxylic acid (2-methylsulfanyl-phenyl)-amide;
  4-(3-phenyl-[1,2,4]thiadiazol-5-yl)-piperazine-1-carboxylic acid (3-methoxy-phenyl)-amide;
  4-(3-phenyl-[1,2,4]thiadiazol-5-yl)-piperazine-1-carboxylic acid biphenyl-4-ylamide;
  4-(3-phenyl-[1,2,4]thiadiazol-5-yl)-piperazine-1-carboxylic acid naphthalen-2-ylamide;
  4-(3-phenyl-[1,2,4]thiadiazol-5-yl)-piperazine-1-carboxylic acid (4-ethoxy-phenyl)-amide;
  4-(3-p-tolyl-[1,2,4]thiadiazol-5-yl)-piperazine-1-carboxylic acid phenylamide;
  4-[3-(4-methoxy-phenyl)-[1,2,4]thiadiazol-5-yl]-piperazine-1-carboxylic acid phenylamide;
  4-[3-(4-chloro-phenyl)-[1,2,4]thiadiazol-5-yl]-piperazine-1-carboxylic acid phenylamide;
  4-(3-phenyl-[1,2,4]thiadiazol-5-yl)-piperazine-1-carboxylic acid (2-fluoro-phenyl)-amide;
  4-(3-phenyl-[1,2,4]thiadiazol-5-yl)-piperazine-1-carboxylic acid (4-chloro-phenyl)-amide;
  4-(3-phenyl-[1,2,4]thiadiazol-5-yl)-piperazine-1-carboxylic acid (2-isopropyl-phenyl)-amide;
  4-(3-phenyl-[1,2,4]thiadiazol-5-yl)-piperazine-1-carboxylic acid (2-trifluoromethyl-phenyl)-amide;
  4-(3-phenyl-[1,2,4]thiadiazol-5-yl)-piperazine-1-carboxylic acid (4-nitro-phenyl)-amide;
  4-(3-phenyl-[1,2,4]thiadiazol-5-yl)-piperazine-1-carboxylic acid (4-dimethylamino-phenyl)-amide;
  4-(3-piperidin-1-yl-[1,2,4]thiadiazol-5-yl)-piperazine-1-carboxylic acid phenylamide;
  4-(3-pyrrolidin-1-yl-[1,2,4]thiadiazol-5-yl)-piperazine-1-carboxylic acid phenylamide;
  4-[3-(4-methyl-piperidin-1-yl)-[1,2,4]thiadiazol-5-yl]-piperazine-1-carboxylic acid phenylamide;
  4-{[4-(3-phenyl-[1,2,4]thiadiazol-5-yl)-piperazine-1-carbonyl]-amino}-benzoic acid methyl ester;
  4-(3-phenyl-[1,2,4]thiadiazol-5-yl)-piperazine-1-carboxylic acid pyrimidin-2-ylamide;
  4-(3-phenyl-[1,2,4]thiadiazol-5-yl)-piperazine-1-carboxylic acid thiazol-2-ylamide;
  4-(3-phenyl-[1,2,4]thiadiazol-5-yl)-piperazine-1-carboxylic acid pyridin-4-ylamide;
  4-(3-phenyl-[1,2,4]thiadiazol-5-yl)-piperazine-1-carboxylic acid pyridin-2-ylamide;
  4-(3-phenyl-[1,2,4]thiadiazol-5-yl)-piperazine-1-carboxylic acid pyridin-3-ylamide;
  4-[3-(4-fluoro-phenyl)-[1,2,4]thiadiazol-5-yl]-piperazine-1-carboxylic acid phenylamide;
  4-[3-(3-nitro-phenyl)-[1,2,4]thiadiazol-5-yl]-piperazine-1-carboxylic acid phenylamide;
  4-(3-m-tolyl-[1,2,4]thiadiazol-5-yl)-piperazine-1-carboxylic acid phenylamide;

4-[3-(3,5-dichloro-phenyl)-[1,2,4]thiadiazol-5-yl]-piperazine-1-carboxylic acid phenylamide;
4-(3-furan-2-yl-[1,2,4]thiadiazol-5-yl)-piperazine-1-carboxylic acid phenylamide;
4-(3-furan-3-yl-[1,2,4]thiadiazol-5-yl)-piperazine-1-carboxylic acid phenylamide;
4-(3-thiophen-2-yl-[1,2,4]thiadiazol-5-yl)-piperazine-1-carboxylic acid phenylamide;
4-(3-thiophen-3-yl-[1,2,4]thiadiazol-5-yl)-piperazine-1-carboxylic acid phenylamide; and
4-(3-morpholin-4-yl-[1,2,4]thiadiazol-5-yl)-piperazine-1-carboxylic acid phenylamide;
and pharmaceutically acceptable salts thereof.

* * * * *